US010544396B2

(12) United States Patent
Yuasa et al.

(10) Patent No.: US 10,544,396 B2
(45) Date of Patent: Jan. 28, 2020

(54) METHOD FOR PRODUCING HIGH-QUALITY IPS CELLS

(71) Applicant: Heartseed Inc., Tokyo (JP)

(72) Inventors: Shinsuke Yuasa, Tokyo (JP); Keiichi Fukuda, Tokyo (JP); Akira Kunitomi, Tokyo (JP)

(73) Assignee: Heartseed Inc., Tokyo (JP)

( * ) Notice: Subject to any disclaimer, the term of this patent is extended or adjusted under 35 U.S.C. 154(b) by 32 days.

(21) Appl. No.: 15/737,988

(22) PCT Filed: Jul. 11, 2016

(86) PCT No.: PCT/JP2016/003282
§ 371 (c)(1),
(2) Date: Dec. 19, 2017

(87) PCT Pub. No.: WO2017/010080
PCT Pub. Date: Jan. 19, 2017

(65) Prior Publication Data
US 2018/0298346 A1    Oct. 18, 2018

(30) Foreign Application Priority Data
Jul. 10, 2015    (JP) ................. 2015-138645

(51) Int. Cl.
C12N 5/074    (2010.01)
C07K 14/47    (2006.01)
C12N 15/01    (2006.01)

(52) U.S. Cl.
CPC ........ C12N 5/0696 (2013.01); C07K 14/4702 (2013.01); C12N 15/01 (2013.01); C12N 2501/602 (2013.01); C12N 2501/603 (2013.01); C12N 2501/604 (2013.01); C12N 2501/605 (2013.01)

(58) Field of Classification Search
CPC ........ C12N 5/0696; C12N 5/10; C12N 15/01; C12N 15/09; C12N 2501/602; C12N 2501/603; C12N 2501/604; C12N 2501/605; C07K 14/4702; C07K 14/47
See application file for complete search history.

(56) References Cited

U.S. PATENT DOCUMENTS

2007/0155013 A1    7/2007    Akaike et al.
2009/0068742 A1    3/2009    Yamanaka et al.
2014/0011279 A1    1/2014    Yamanaka et al.
2015/0184131 A1    7/2015    Wu et al.

FOREIGN PATENT DOCUMENTS

JP    2011004674    1/2011
JP    2014217344    11/2014
JP    2014217345    11/2014
RU    2375448    12/2009
RU    2458983    8/2012
WO    2009114949    9/2009

OTHER PUBLICATIONS

Takahashi et al., Cell, 131: 12-12, Nov. 30, 2007.*
Reubinoff et al. (2000, Nature Biotechnology, vol. 18, pp. 399-404.*
Reijo et al. (2009, Differentiation, vol. 78, pp. 18-23).*
Dr. Lyle Armstrong to the UK House of Parliaments' Select Committee on Science and Technology, Fifth Report of Session Jul. 2006, vol. II, pp. 76-77, Apr. 5, 2007.*
Lai et al., Proc Natl Acad Sci U S A. Mar. 6, 2012; 109(10):3772-7.*
Dominiguez-Bendala et al., Handbook of Stem Cells, Chapter 70: Islet Cell Therapy and Pancreatic Stem Cells, pp. 835-853, 2013.*
Yu et al., Science, 324(5928): 797-801, 2009.*
Thomson, Science, 282: 1145-1147, 1998.*
Kim et al., Cell, 136: 411-419, 2009.*
Kim et al. Cell Stem Cell, 4(6): 472-476, 2009.*
Zhou et al., Cell Stem Cell, 4: 381-384, 2009.*
Choi et al., Scientific Reports, 5: 1-8, 2015.*
Kunitomi, Akira, Shinsuke Yuasa, Fumihiro Sugiyama, Yuki Saito, Tomohisa Seki, Dai Kusumoto, Shin Kashimura et al. "H1foo has a pivotal role in qualifying induced pluripotent stem cells." Stem cell reports 6, No. 6 (2016): 825-833.
Awe, Jason P., and James A. Byrne. "Identifying candidate oocyte reprogramming factors using cross-species global transcriptional analysis." Cellular reprogramming 15, No. 2 (2013): 126-133.
Maekawa, Momoko, Kei Yamaguchi, Tomonori Nakamura, Ran Shibukawa, Ikumi Kodanaka, Tomoko Ichisaka, Yoshifumi Kawamura, Hiromi Mochizuki, Naoki Goshima, and Shinya Yamanaka. "Direct reprogramming of somatic cells is promoted by maternal transcription factor Glis1." Nature 474, No. 7350 (2011): 225.
Shinagawa, Toshie, Tsuyoshi Takagi, Daisuke Tsukamoto, Chinatsu Tomaru, Linh My Huynh, Padavattan Sivaraman, Thirumananseri Kumarevel et al. "Histone variants enriched in oocytes enhance reprogramming to induced pluripotent stem cells." Cell stem cell 14, No. 2 (2014): 217-227.
Brink, Thore C., Smita Sudheer, Doreen Janke, Justyna Jagodzinska, Marc Jung, and James Adjaye. "The origins of human embryonic stem cells: a biological conundrum." Cells Tissues Organs 188, No. 1-2 (2008): 9-22.

(Continued)

Primary Examiner — Thaian N Ton
(74) Attorney, Agent, or Firm — Occhiuti & Rohlicek LLP

(57) ABSTRACT

An object of the present invention is to provide an agent for improving quality of an iPS cell, a method for producing an iPS cell, an iPS cell produced by such a method for production, and a composition for producing an iPS cell. The method for producing an iPS cell according to the present invention comprises the step of introducing (a) a nuclear reprogramming substance and (b) an H1foo gene or a gene product thereof into a somatic cell. High-quality iPS cells can be produced in greater quantity by introducing not only a nuclear reprogramming substance but also an H1foo gene or a gene product thereof into a somatic cell.

4 Claims, 12 Drawing Sheets
Specification includes a Sequence Listing.

(56) References Cited

OTHER PUBLICATIONS

Hayakawa, Koji, Jun Ohgane, Satoshi Tanaka, Shintaro Yagi, and Kunio Shiota. "Oocyte-specific linker histone H1foo is an epigenomic modulator that decondenses chromatin and impairs pluripotency." Epigenetics 7, No. 9 (2012): 1029-1036.

Nashun, Buhe, Peter WS Hill, and Petra Hajkova. "Reprogramming of cell fate: epigenetic memory and the erasure of memories past." The EMBO journal (2015): e201490649, pp. 1296-1308.

Takahashi, Kazutoshi, and Shinya Yamanaka. "Induction of pluripotent stem cells from mouse embryonic and adult fibroblast cultures by defined factors." cell 126, No. 4 (2006): 663-676.

Steinbach, Oliver C., Alan P. Wolffe, and Ralph AW Rupp. "Somatic linker histones cause loss of mesodermal competence in Xenopus." Nature 389, No. 6649 (1997): 395, Abstract only, 1 page.

Hebbar, Pratibha B., and Trevor K. Archer. "Altered histone H1 stoichiometry and an absence of nucleosome positioning on transfected DNA." Journal of Biological Chemistry 283, No. 8 (2008): 4595-4601.

Notification of Transmittal of Translation of the International Preliminary Report on Patentability, and the Translation of the International Preliminary Report on Patentability, issued by the International Bureau of WIPO dated Jan. 25, 2018, for International Application No. PCT/JP2016/003282, 6 page.

Shinya Yamanaka. "Induced Pluripotent Stem Cells: Past, Present, and Future", Cell Stem Cell, vol. 10, No. 6, Jun. 14, 2012, pp. 678-684, XP028492653, ISSN: 1934-5909, DOI: 10.1016/J.Stem. 2012.05.005 [retrieved on May 3, 2012].

Mattout Anna et al: "Global epigenetic changes during somatic cell reprogramming to iPS cells", Journal of Molecular Cell Biology, vol. 3, No. 6, Dec. 2011, pp. 341-350, XP002786431, ISSN: 1674-2788, DOI: 10.1093/JMCB/MJR028.

Yun Yan et al.: "H1foo is essential for in vitro meiotic maturation of bovine oocytes", Zygote, vol. 23, No. 3, Jun. 2015, pp. 416-425, XP00276432, ISSN: 0967-1994, DOI: 10.1017/S0967199414000021.

Yamanaka, S. et al., "Nuclear Reprogramming to a Pluripotent State by Three Approaches," Nature; 2010; vol. 465, pp. 704-712.

Becker, Matthias et al. Molecular Biology of the Cell, Aug. 2005, vol. 16, No. 8, pp. 3887-3895.

\* cited by examiner

[Figure 1]
a
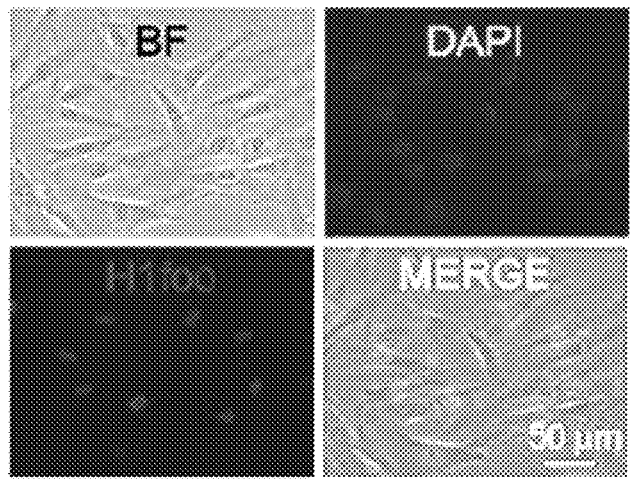
b
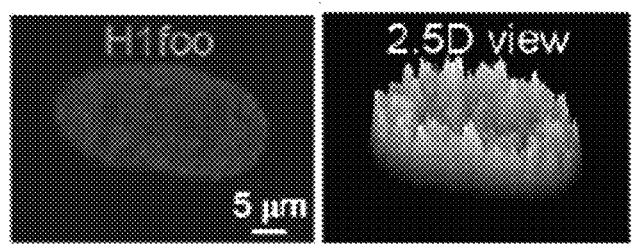
c
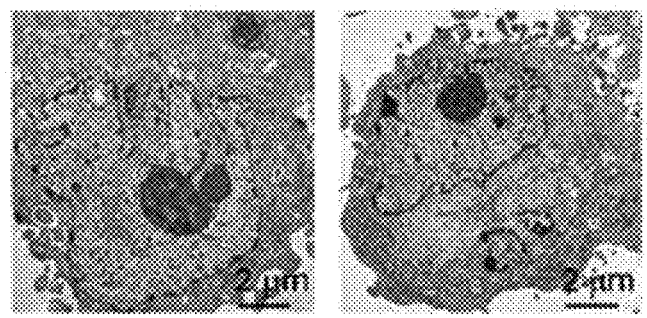

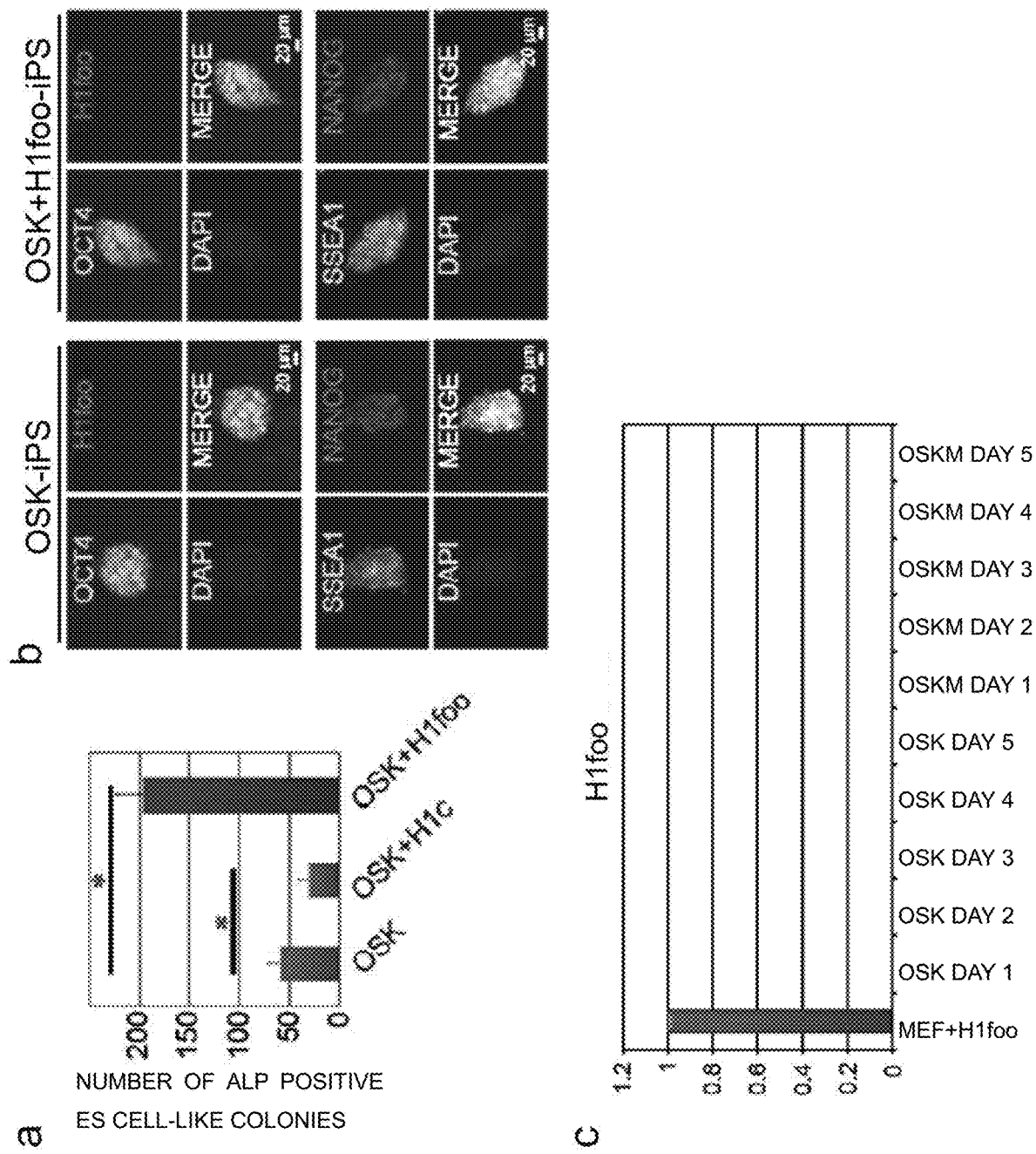

[Figure 3]
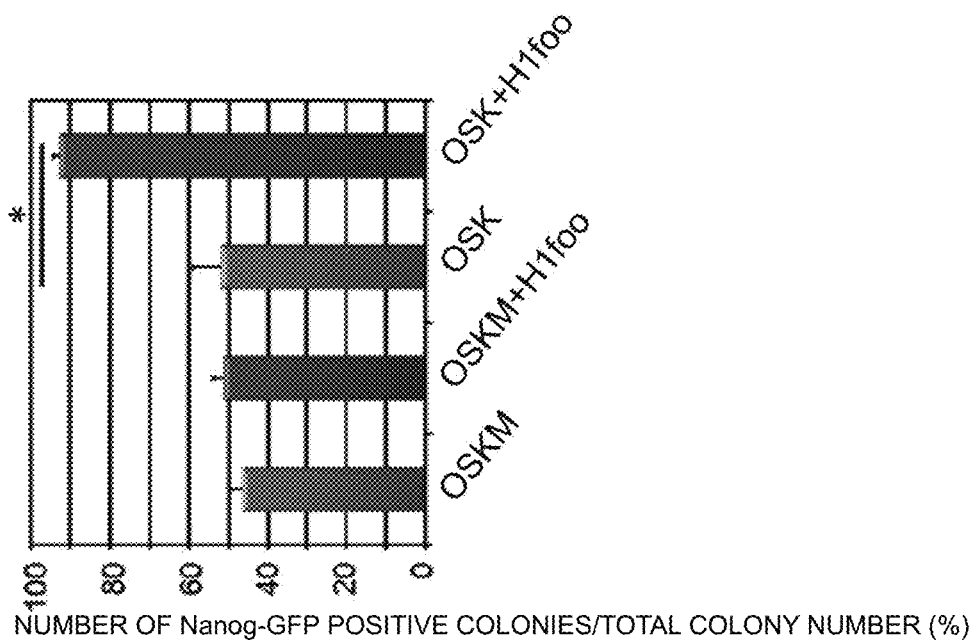
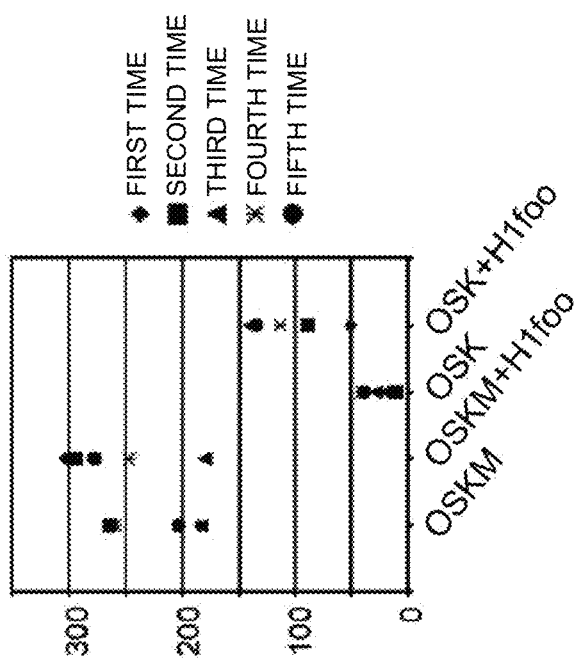
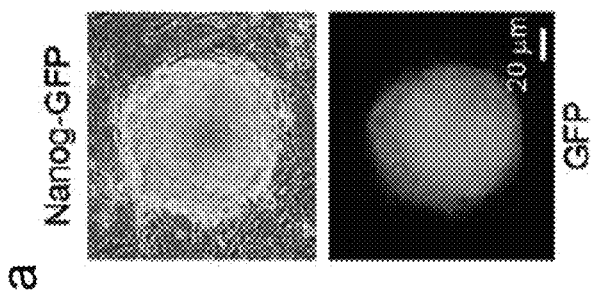

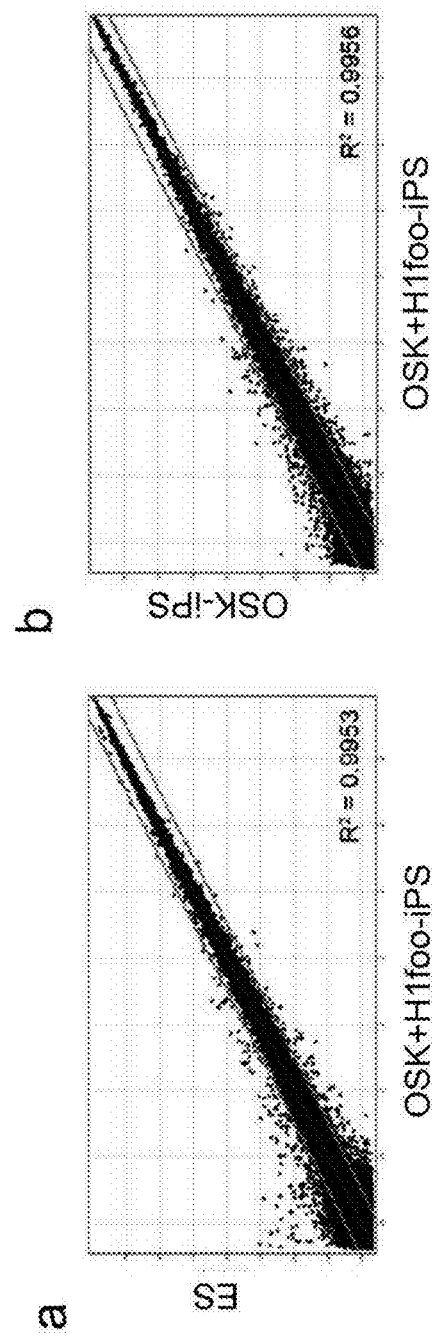
[Figure 4]

[Figure 5]
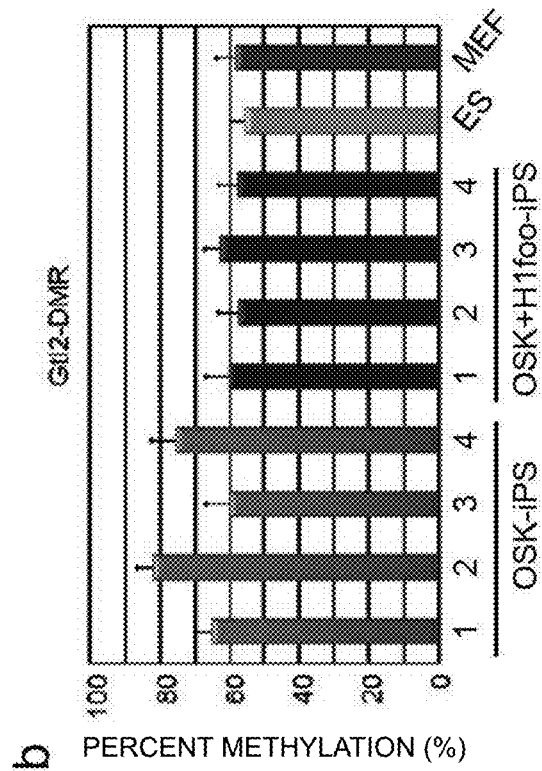
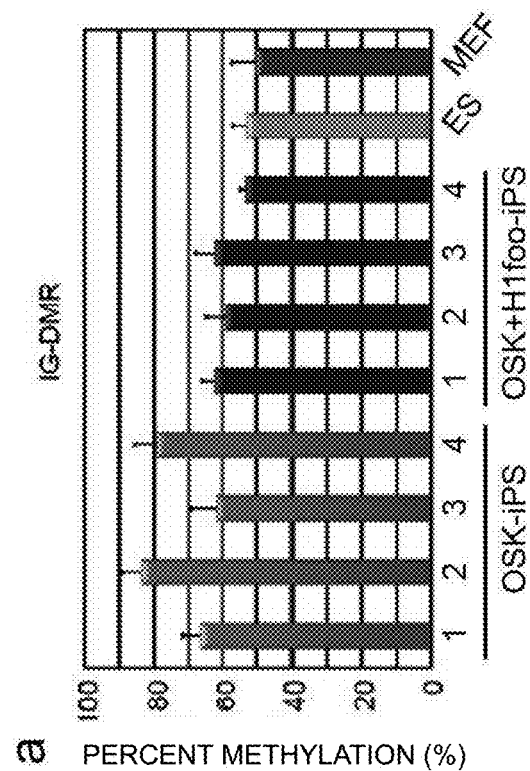

[Figure 6]
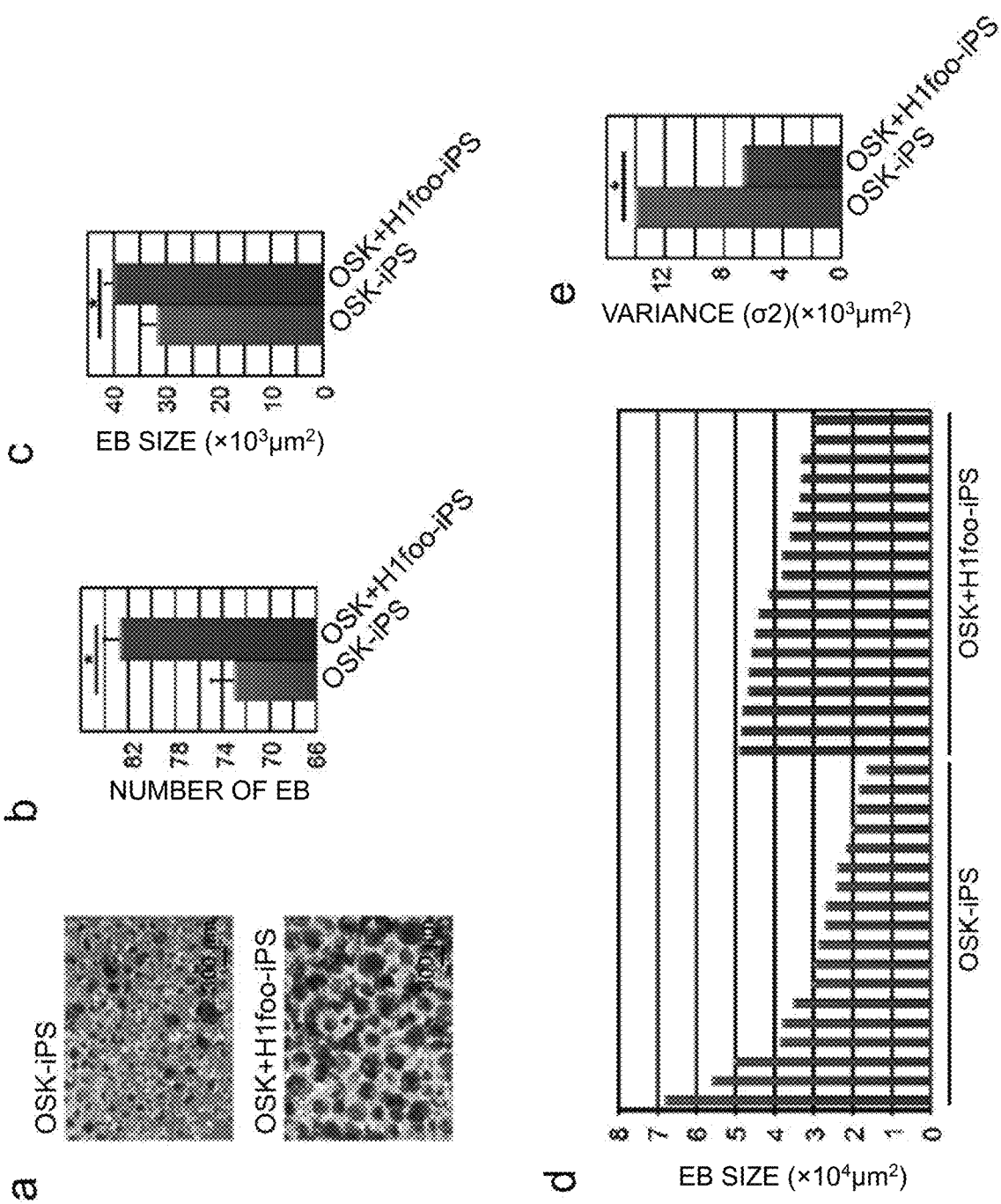

[Figure 7]
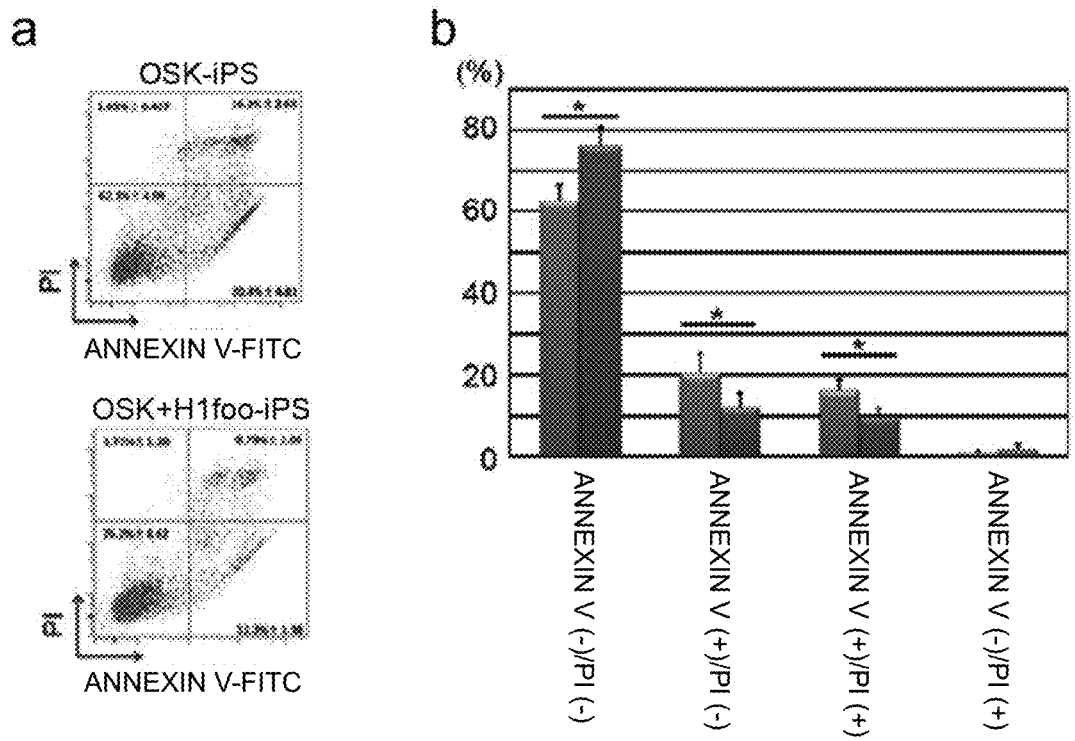
[Figure 8]
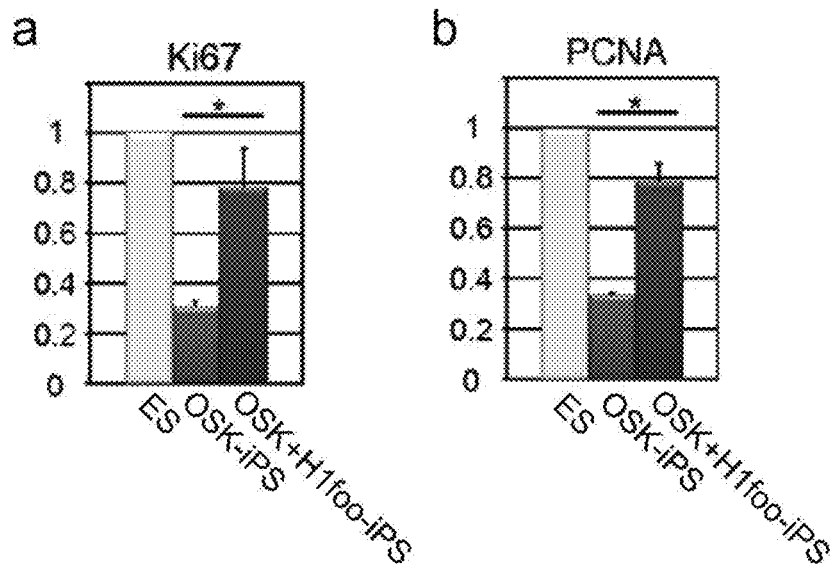

[Figure 9]
a
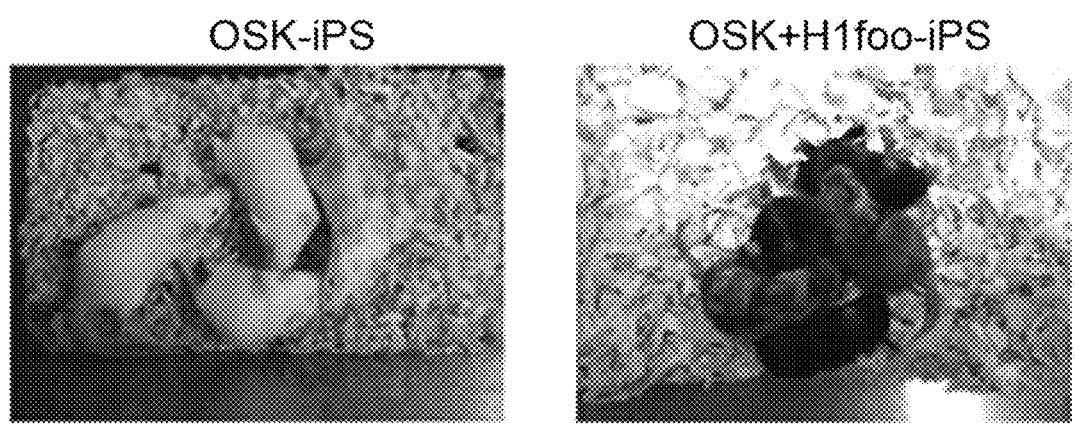
b
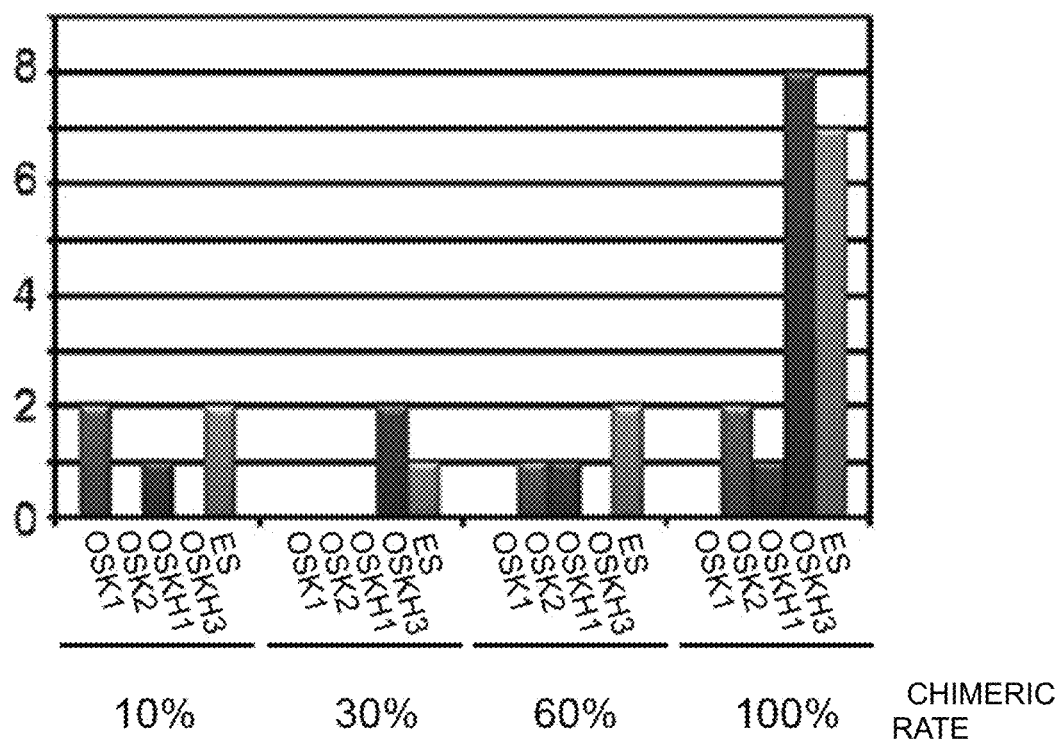

[Figure 10]
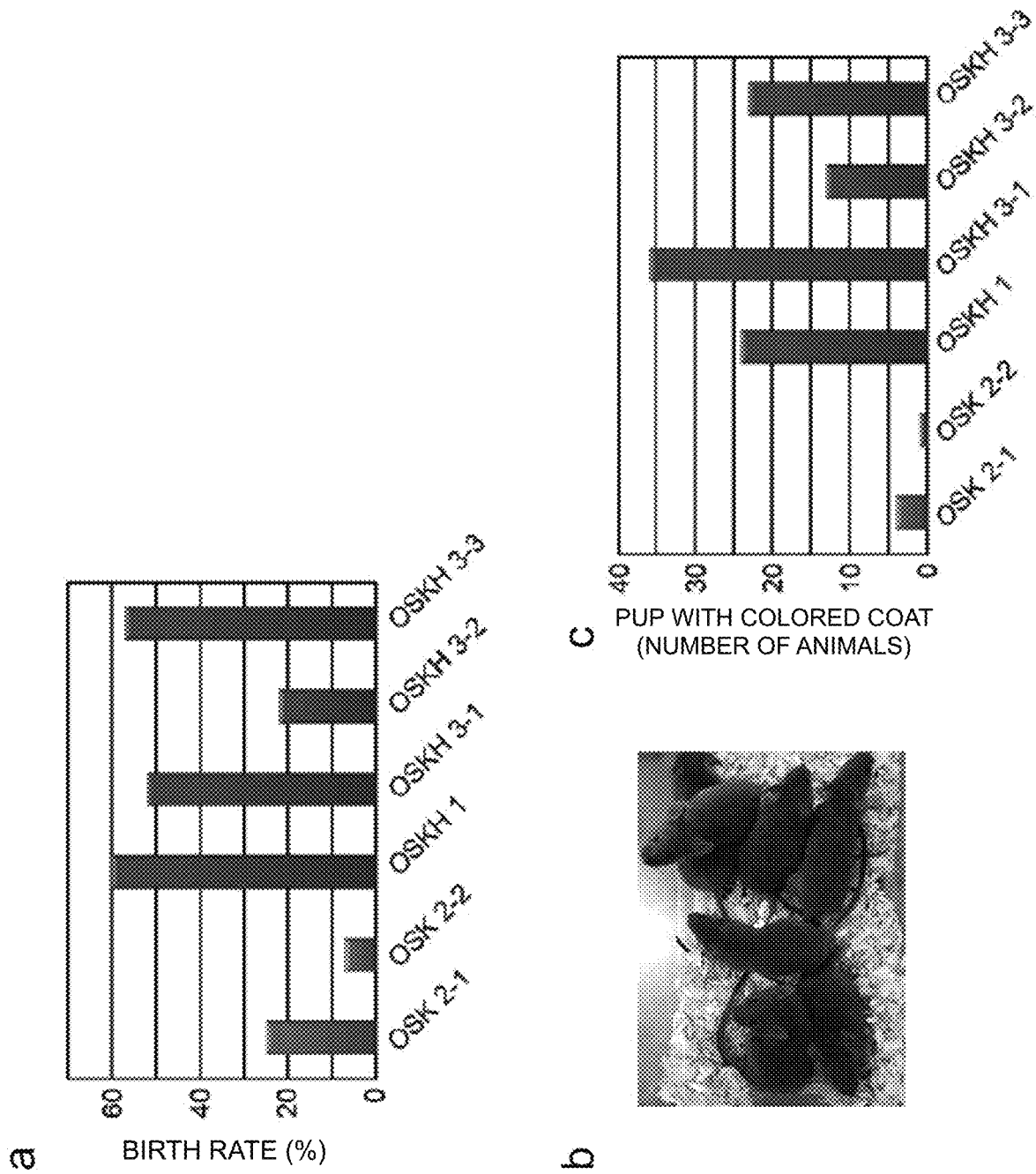

[Figure 11]
a
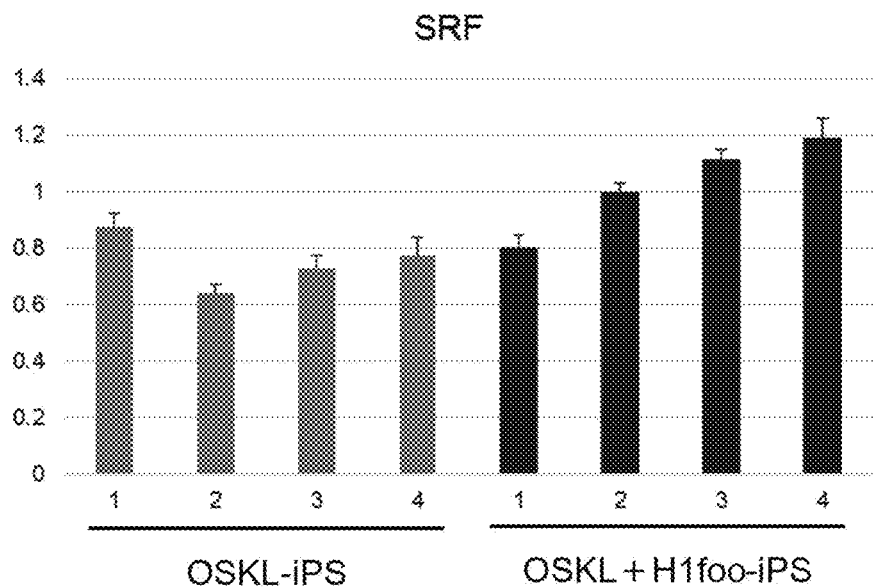
b
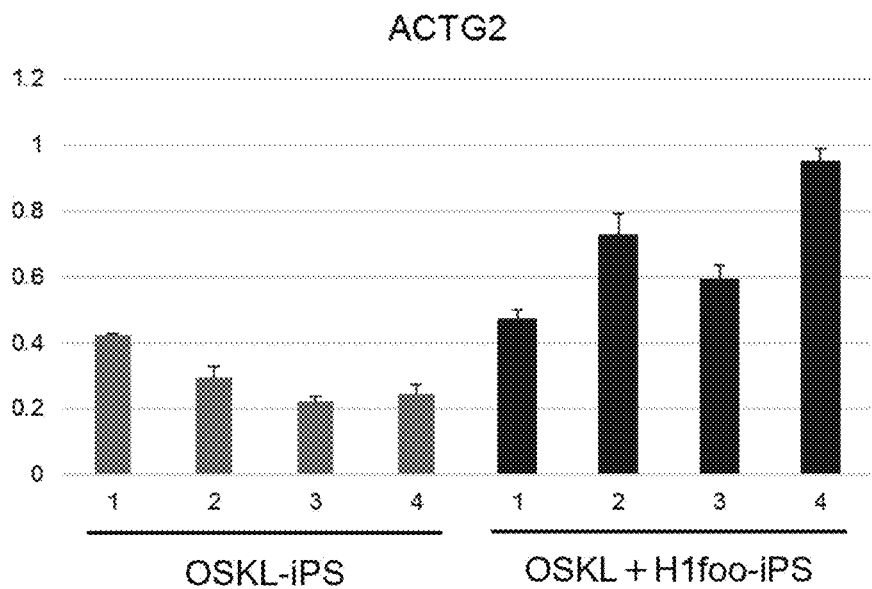

[Figure 12]
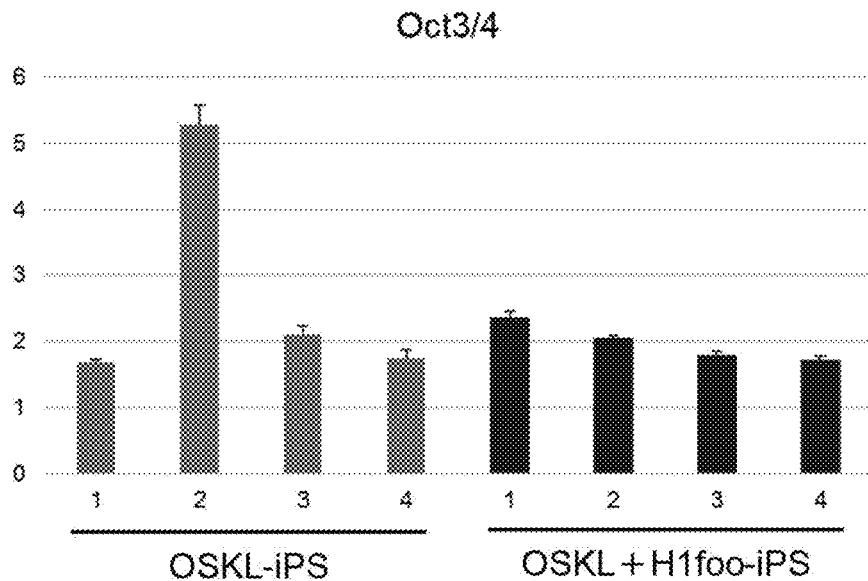
[Figure 13]
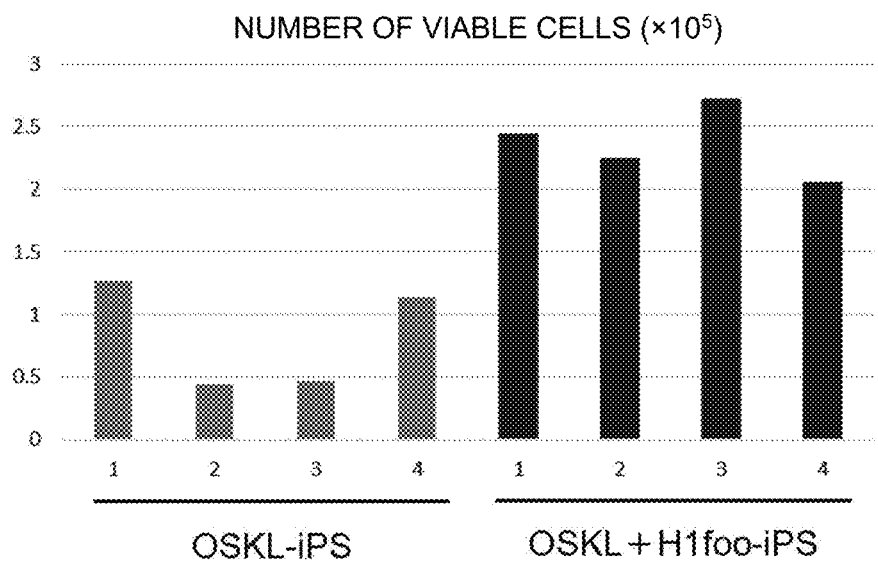

[Figure 14]
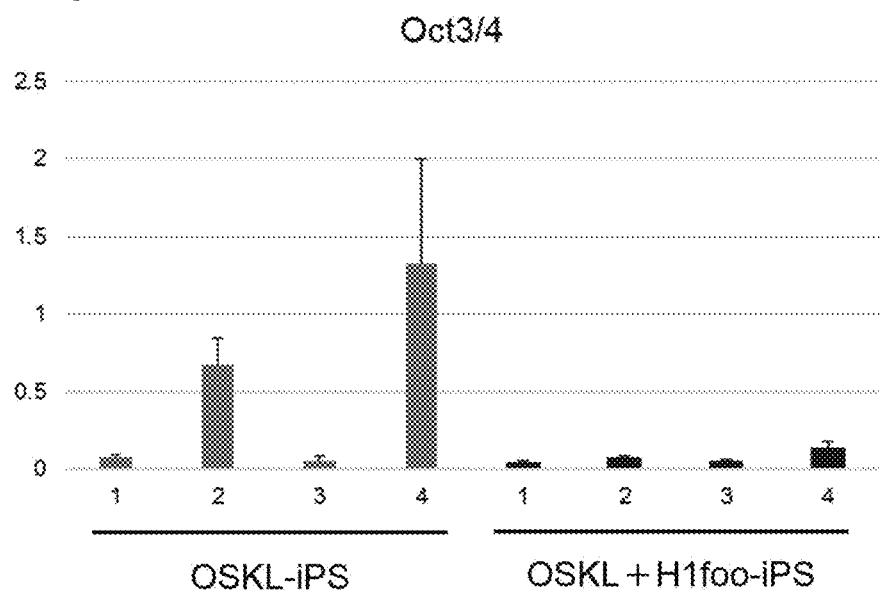

METHOD FOR PRODUCING HIGH-QUALITY IPS CELLS

CROSS REFERENCE TO RELATED APPLICATIONS

This application is a National Stage of International Application No. PCT/JP2016/003282 filed on Jul. 11, 2016, which claims priority to Japanese Application No. 2015-138645 filed Jul. 10, 2015, the contents of which are hereby incorporated by reference in their entirety.

TECHNICAL FIELD

The present invention relates to an agent for improving quality of an iPS cell, a method for producing an iPS cell, an iPS cell produced by such a method for production, and a composition for producing an iPS cell.

BACKGROUND ART

Induced pluripotent stem (iPS) cells can be produced from somatic cells by introducing Oct3/4, Sox2, Klf4, and c-Myc (Non-patent Document 1, Patent Document 1). This can be achieved by reprogramming the parent somatic cell transcription network and epigenetic signatures. iPS cells bring various benefits for basic research, drug innovation, and regenerative medicine. However, it is still a serious problem that cell populations of produced iPS cells are more heterogeneous in quality than cell populations of embryonic-stem cells (ES cells). For example, while ES cells have small variance in property among cells and substantially any cell can be differentiated into the intended cell, iPS cells have large variance in property among cells and there have often been cells that cannot been differentiated into the intended cell. It is important for basic studies and the clinical purpose that any iPS cell displays high quality without variance.

Many attempts have been made to solve the problem that cell populations of iPS cells are heterogeneous in quality. For example, Patent Document 2 discloses that the production efficiency and stability of iPS cells can be improved by the predetermined number of times of introduction of a predetermined amount of an Oct3/4 gene, a Klf4 gene, a c-Myc gene, and a Sox2 gene into somatic cells. Moreover, Patent Document 3 discloses that induced pluripotent stem cells (iPS cells) excellent in quality can be produced efficiently in a short period of time by introducing into somatic cells a Prdm14 gene or a gene product thereof, an Esrrb gene or a gene product thereof, and a Sall4a gene or a gene product thereof, in addition to an Oct3/4 gene or a gene product thereof, a Sox2 gene or a gene product thereof, a Klf4 gene or a gene product thereof, and a c-Myc gene or a gene product thereof. Furthermore, Patent Document 4 discloses that induced pluripotent stem cells (iPS cells) excellent in quality can be produced efficiently in a short period of time by introducing into somatic cells a Jarid2 mutant gene or a gene product thereof in addition to an Oct3/4 gene or a gene product thereof, a Sox2 gene or a gene product thereof, a Klf4 gene or a gene product thereof, and a c-Myc gene or a gene product thereof. However, there has been still room for improvement in quality of iPS cells. Therefore, the development of a method for producing high-quality iPS cells with smaller variance in quality has been demanded.

The linker histone H1 family binds to linker DNA and generates higher-order chromatin structures to control gene expression. The members of the linker histone H1 family include histones H1a, H1b, H1c, H1d, H1e, H1foo, H1x, H1.0, H1t, H1T2, and HILS1. Most members of the linker histone family are somatic linker histones that condense chromatin. Accordingly, such structures generally repress general gene transcription activity (Non-patent Documents 2 and 3).

PRIOR ART DOCUMENTS

Patent Documents

Patent Document 1: Japanese Patent No. 4183742
Patent Document 2: Japanese unexamined Patent Application Publication No. 2011-004674
Patent Document 3: Japanese unexamined Patent Application Publication No. 2014-217344
Patent Document 4: Japanese unexamined Patent Application Publication No. 2014-217345

Non-Patent Documents

Non-patent Document 1: Takahashi, K. & Yamanaka, S. Induction of pluripotent stem cells from mouse embryonic and adult fibroblast cultures by defined factors. Cell 126, 663-676 (2006)
Non-patent Document 2: Steinbach, O. C., Wolffe, A. P. & Rupp, R. A. Somatic linker histones cause loss of mesodermal competence in *Xenopus*. Nature 389, 395-399 (1997)
Non-patent Document 3: Hebbar, P. B. & Archer, T. K. Altered histone H1 stoichiometry and an absence of nucleosome positioning on transfected DNA. The Journal of biological chemistry 283, 4595-4601 (2008).

SUMMARY OF THE INVENTION

Object to be Solved by the Invention

An object of the present invention is to provide an agent for improving quality of an iPS cell, a method for producing an iPS cell, an iPS cell produced by such a method for production, and a composition for producing an iPS cell.

Means to Solve the Object

The present inventors have studied diligently to improve quality of iPS cells and found as a result that in a method for producing an iPS cell by introducing a nuclear reprogramming substance into a somatic cell, introducing not only the nuclear reprogramming substance, but also "an H1foo gene or a gene product thereof" into the somatic cell allows the production of high-quality iPS cells with smaller variance in quality, thereby completing the present invention. It was unexpected for those skilled in the art that the combination of the "H1foo gene or gene product thereof" and the nuclear reprogramming substance allowed the production of high-quality iPS cells with smaller variance in quality.

Accordingly, the invention provides:
(1) an agent for improving quality of an iPS cell, comprising an H1foo gene or a gene product thereof; and
(2) the agent for improving quality of an iPS cell according to (1), wherein the agent comprises an expression vector comprising the H1foo gene.

Moreover, the present invention provides:
(3) a method for producing an iPS cell, comprising the step of introducing (a) a nuclear reprogramming substance and (b) an H1foo gene or a gene product thereof into a somatic cell;

(4) the method for producing an iPS cell according to (3), wherein the nuclear reprogramming substance comprises at least one selected from the group consisting of a gene of Oct gene family, a gene of Sox gene family, a gene of Klf gene family, a gene of Myc gene family, a gene of Lin gene family, a Nanog gene, and gene products thereof;

(5) the method for producing an iPS cell according to (3) or (4), wherein the nuclear reprogramming substance consists of a gene of Oct gene family or a gene product thereof, a gene of Sox gene family or a gene product thereof, and a gene of Klf gene family or a gene product thereof;

(6) the method for producing an iPS cell according to any one of (3) to (5), wherein the nuclear reprogramming substance consists of an Oct3/4 gene or a gene product thereof, a Sox2 gene or a gene product thereof, and a Klf4 gene or a gene product thereof; and (7) the method for producing an iPS cell according to any one of (3) to (5), wherein the nuclear reprogramming substance consists of an Oct3/4 gene or a gene product thereof, a Sox2 gene or a gene product thereof, a Klf4 gene or a gene product thereof, and an L-Myc gene or a gene product thereof.

Furthermore, the invention provides:

(8) an iPS cell produced by the method for producing an iPS cell according to any one of (1) to (7); and (9) a composition for producing an iPS cell, comprising (a) a nuclear reprogramming substance and (b) an H1foo gene or a gene product thereof.

Effect of the Invention

The present invention can provide an agent for improving quality of an iPS cell, a method for producing an iPS cell, an iPS cell produced by such a method for production, and a composition for producing an iPS cell. According to the present invention, high-quality iPS cells with smaller variance in quality can be produced.

BRIEF DESCRIPTION OF DRAWINGS

FIG. 1 is a set of microscopic images of tail tip fibroblasts (hereinafter simply referred to as "mouse fibroblasts") of a C57BL/6J mouse expressing exogenous (mouse) H1foo. The "BF", "DAPI", "H1foo", and "MERGE" images in FIG. 1a indicate a phase contrast image, a DAPI fluorescent staining image, an H1foo fluorescent staining image, and an overlay image of the 3 images. The left and right images in FIG. 1b are H1foo fluorescent staining 2 dimension and 2.5 dimension images, respectively. The left and right images in FIG. 1c are electron microscopic images of control cells (mouse fibroblasts) and mouse fibroblasts expressing exogenous H1foo, respectively.

FIG. 2a shows the results of introducing 3 kinds of nuclear reprogramming substances (mouse Oct3/4, Sox2, and Klf4 genes, [OSK gene]), OSK genes and a linker histone H1 gene (OSK+H1c genes) or OSK genes and an H1foo gene (OSK+H1foo genes) into mouse fibroblasts and analyzing the colonization efficiency of ALP-positive ES-like cells (iPS cells). FIG. 2b shows the results of analyzing the expression of 3 kinds of pluripotent markers (Oct3/4, Nanog, and SSEA1) in iPS cells produced by introducing the OSK genes or the OSK+H1foo genes (hereinafter referred to as "OSK-iPS cells" and "OSK+H1foo-iPS cells", respectively). FIG. 2c shows the results of analyzing the endogenous H1foo expression 1 to 5 days after the introduction of the OSK genes or the OSK genes and a c-Myc gene (OSKM genes). "MEF+H1foo" in FIG. 2c shows the results of analyzing mouse embryonic fibroblasts (MEF) in which an H1foo gene is introduced.

FIG. 3 shows the results of introducing OSKM genes, OSKM genes and an H1foo gene (OSKM+H1foo genes), OSK genes, or OSK+H1foo genes into Nanog-GFP expressing fibroblasts and analyzing the percentage of Nanog-GFP-positive ES-like cells (iPS cells).

FIG. 4a shows the results of comparing global gene transcriptome profiles of the OSK+H1foo-iPS cells and ES cells. FIG. 4b shows the results of comparing global gene transcriptome profiles of the OSK+H1foo-iPS cells and the OSK-iPS cells.

FIG. 5 shows the results of analyzing DNA methylation levels in IG-DMR (FIG. 5a) and Gtl2-DMR (FIG. 5b) in OSK-iPS cells and OSK+H1foo-iPS cells. "ES" and "MEF" in the figure indicate the results of analyzing ES cells and MEF cells, respectively.

FIG. 6 shows the results of analyzing the morphology of embryoid bodies (EBs) formed from OSK-iPS cells and OSK+H1foo-iPS cells.

FIG. 7 shows the results of analyzing the percentage of apoptotic cells in EBs formed from OSK-iPS cells and OSK+H1foo-iPS cells.

FIG. 8 shows the results of analyzing the expression of 2 cell proliferation markers (Ki67 and PCNA) in EBs formed from OSK-iPS cells and OSK+H1foo-iPS cells.

FIG. 9 shows the results of analyzing the chimera competency of OSK-iPS cells and the OSK+H1foo-iPS cells.

FIG. 10 shows the results of analyzing germline transmission potential of chimera mice derived from OSK-iPS cells and OSK+H1foo-iPS cells.

FIG. 11 shows the results of quantitative RT-PCR analysis of the SRF gene (FIG. 11a) and the ACTG2 gene (FIG. 11b) in OSKL+H1foo-iPS cells (iPS cells produced by introducing Oct3/4, Sox2, Klf4, L-Myc, and H1foo genes) and OSKL-iPS cells (iPS cells produced by introducing Oct3/4, Sox2, Klf4, and L-Myc genes). The numbers 1 to 4 on the abscissa of the graph indicate the clone numbers.

FIG. 12 shows the results of quantitative RT-PCR analysis of the Oct3/4 gene in OSKL+H1foo-iPS cells and OSKL-iPS cells. The numbers 1 to 4 on the abscissa of the graph indicate the clone numbers.

FIG. 13 shows the numbers of viable cells after 5 days of culturing OSKL+H1foo-iPS cells and OSKL-iPS cells with induction of differentiation. The numbers 1 to 4 on the abscissa axis of the graph indicate the clone numbers.

FIG. 14 shows the results of quantitative RT-PCR analysis of the Oct3/4 gene after culturing OSKL+H1foo-iPS cells and OSKL-iPS cells for 5 days with induction of differentiation. The numbers 1 to 4 on the abscissa axis of the graph indicate the clone numbers.

MODE OF CARRYING OUT THE INVENTION

1. Method for Producing iPS Cell

The method for producing an iPS cell according to the present invention comprises at least the step of: introducing (a) a nuclear reprogramming substance and (b) an H1foo gene or a gene product thereof into a somatic cell (hereinafter also referred to simply as the "introduction step".) and may further comprise another step as needed.

<Introduction Step>

The introduction step is at least the step of introducing (a) a nuclear reprogramming substance and (b) an H1foo gene or a gene product thereof into a somatic cell. By introducing not only a nuclear reprogramming substance, but also an H1foo gene or a gene product thereof into a somatic cell, a larger amount of high-quality iPS cells can be produced. As used herein, the gene product means a messenger RNA (mRNA) transcribed from a gene and/or a protein translated from the mRNA. The H1foo gene means a polynucleotide encoding an H1foo protein. The H1foo gene or a gene product thereof can be used as an agent for improving quality of an iPS cell. Moreover, a vector comprising an H1foo gene, which is described later, can be also used as an agent for improving quality of an iPS cell.

(H1foo Gene)

The source of the H1foo gene is not particularly limited, but may be appropriately selected according to the purpose and examples include any mammal such as a human, a mouse, a rat, a cow, a sheep, a horse, and a monkey. The sequence information of the H1foo gene can be obtained from a publically known database and can be obtained, for example, under accession number BC047943 (human), AY158091 (human), or BC137916 (mouse) in the GenBank. The nucleotide sequence of an human H1foo gene (BC047943) is set forth in SEQ ID No: 1 and the amino acid sequence of an human H1foo protein (the protein encoded by the H1foo gene of BC047943) is set forth in SEQ ID No: 2. The nucleotide sequence of an human H1foo gene (AY158091) is set forth in SEQ ID No: 59 and the amino acid sequence of an human H1foo protein (the protein encoded by the H1foo gene of AY158091) is set forth in SEQ ID No: 60. The nucleotide sequence of an mouse H1foo gene (BC137916) is set forth in SEQ ID No: 3 and the amino acid sequence of an mouse H1foo protein (the protein encoded by the H1foo gene of BC137916) is set forth in SEQ ID No: 4.

The nucleotide sequences of the H1foo genes and the nucleotide sequences of the mRNAs thereof may be the same as the nucleotide sequences of the wild-type H1foo genes and the nucleotide sequences of the mRNAs thereof or may comprise a mutation. Examples of such a nucleotide sequence comprising a mutation include a "nucleotide sequence that is modified from a nucleotide sequence of a wild-type H1foo gene (for example, a nucleotide sequence set forth in SEQ ID No: 1 or 59 or 3) or the nucleotide sequence of the mRNA thereof by a deletion, a substitution, an insertion, or an addition of 1 to 30, preferably 1 to 20, more preferably 1 to 15, more preferably 1 to 10, more preferably 1 to 5, more preferably 1 to 3 nucleotides and encodes a protein having the H1foo activity" and a "nucleotide sequence that comprises in the part to be translated into a protein, a nucleotide sequence having 70% or more, preferably 80% or more, more preferably 85% or more, more preferably 90% or more, more preferably 95% or more, or more preferably 98% or more sequence identity with a nucleotide sequence of a wild-type H1foo gene (for example, a nucleotide sequence set forth in SEQ ID No: 1 or 59 or 3) or the nucleotide sequence of the mRNA thereof, and encodes a protein having the H1foo activity".

The amino acid sequences of the H1foo proteins may be the same as the amino acid sequences of the wild-type H1foo proteins (for example, an amino acid sequence set forth in SEQ ID No: 2 or 60 or 4) or may comprise a mutation. Examples of such a protein comprising a mutation include a "protein that consists of an amino acid sequence modified from an amino acid sequence of a wild-type H1foo protein (for example, an amino acid sequence set forth in SEQ ID No: 2 or 60 or 4) by a deletion, a substitution, an insertion, or an addition of 1 to 30, preferably 1 to 20, more preferably 1 to 15, more preferably 1 to 10, more preferably 1 to 5, or more preferably 1 to 3 amino acids and has the H1foo activity" and a "protein that consists of an amino acid sequence having a 70% or more, preferably 80% or more, more preferably 85% or more, more preferably 90% or more, more preferably 95% or more, or more preferably 98% or more sequence identity with an amino acid sequence of a wild-type H1foo protein (for example, an amino acid sequence set forth in SEQ ID No: 2 or 60 or 4) and has the H1foo activity". As used herein, the "protein that has the H1foo activity" means a protein that allows a larger amount of high-quality iPS cells to be produced when it is introduced into a somatic cell with a nuclear reprogramming substance than the amount when only the nuclear reprogramming substance is introduced into the somatic cell.

(Nuclear Reprogramming Substance)

As used herein, the "nuclear reprogramming substance" means a substance (or a group of substances) that allows the induction of a somatic cell into an iPS cell by introducing the substance singly or a combination of the substance and another substance into the somatic cell. Such a nuclear reprogramming substance may be any substance such as a gene (including one in a form of being incorporated in an expression vector) or a gene product thereof or a low molecular weight compound, as long as it is a substance (or a group of substances) that allows the induction of an iPS cell from a somatic cell. The gene that is a nuclear reprogramming substance means a polynucleotide encoding a protein that is a nuclear reprogramming substance. Examples of the nuclear reprogramming substance when it is a gene or a gene product thereof include at least one selected from the group consisting of: a gene of Oct gene family, a gene of Sox gene family, a gene of Klf gene family, a gene of Myc gene family, a gene of Lin gene family, and a Nanog gene, and gene products thereof (WO2007/69666, Japanese Patent No. 5696282; Science, 2007, 318:1917-1920); in particular, preferably 2 or more and more preferably 3 or more selected from the group, and preferably 2 to 4 and more preferably 3 or 4 selected from the group. Specific examples of genes of these families and combinations thereof are listed below. Although only the gene names are described in the following, use of gene products thereof are also included.

An example may be:

(a) 1 nuclear reprogramming substance consisting of a gene of Oct gene family;

(b) a combination of 2 nuclear reprogramming substances consisting of a gene of Oct gene family and a gene of Sox gene family;

(c) a combination of 2 nuclear reprogramming substances consisting of a gene of Oct gene family and a gene of Klf gene family;

(d) a combination of 2 nuclear reprogramming substances consisting of a gene of Oct gene family and a Nanog gene, (e) a combination of 3 nuclear reprogramming substances consisting of a gene of Oct gene family, a gene of Sox gene family, and a gene of Klf gene family, (f) a combination of 3 nuclear reprogramming substances consisting of a gene of Oct gene family, a gene of Klf gene family, and a gene of Myc gene family;

(g) a combination of 4 nuclear reprogramming substances consisting of a gene of Oct gene family, a gene of Sox gene family, a gene of Klf gene family, and a gene of Myc gene family; and (h) a combination of 4 nuclear reprogramming substances consisting of a gene of Oct gene family, a gene of Sox gene family, a gene of Lin gene family, and a Nanog gene, or a combination of a nuclear reprogramming substance set forth in the (a) to (h) or a combination thereof and a further added other nuclear reprogramming substance (a gene or a gene product thereof).

Specific examples include:

(a') a combination of nuclear reprogramming substances including 1 nuclear reprogramming substance consisting of a gene of Oct gene family;

(b') a combination of nuclear reprogramming substances including 2 nuclear reprogramming substances consisting of a gene of Oct gene family and a gene of Sox gene family;

(c') a combination of nuclear reprogramming substances including 2 nuclear reprogramming substances consisting of a gene of Oct gene family and a gene of Klf gene family;

(d') a combination of nuclear reprogramming substances including 2 nuclear reprogramming substances consisting of a gene of Oct gene family and a Nanog gene;

(e') a combination of nuclear reprogramming substances including 3 nuclear reprogramming substances consisting of a gene of Oct gene family, a gene of Sox gene family, and a gene of Klf gene family;

(f') a combination of nuclear reprogramming substances including 3 nuclear reprogramming substances consisting of a gene of Oct gene family, a gene of Klf gene family, and a gene of Myc gene family;

(g') a combination of nuclear reprogramming substances including 4 nuclear reprogramming substances consisting of a gene of Oct gene family, a gene of Sox gene family, a gene of Klf gene family, and a gene of Myc gene family; and (h') a combination of nuclear reprogramming substances including 4 nuclear reprogramming substances consisting of a gene of Oct gene family, a gene of Sox gene family, a gene of Lin gene family, and a Nanog gene.

More specific examples include, but are not limited to, the following combinations.

(1) an Oct3/4 gene, a Klf4 gene, a c-Myc gene;

(2) an Oct3/4 gene, a Sox2 gene, a Klf4 gene, a c-Myc gene (wherein the Sox2 gene is replaceable with a Sox1 gene, a Sox3 gene, a Sox15 gene, a Sox17 gene, or a Sox18 gene; the Klf4 gene is replaceable with a Klf1 gene, a Klf2 gene, or a Klf5 gene; and the c-Myc gene is replaceable with a T58A (active form mutant) gene, a N-Myc gene, or a L-Myc gene.);

(3) an Oct3/4 gene, a Sox2 gene, a Klf4 gene, a c-Myc gene, an Fbx15 gene, a Nanog gene, an Eras gene, an ECAT15-2 gene, a Tcl1 gene, β-catenin (active form mutant S33Y);

(4) an Oct3/4 gene, a Sox2 gene, a Klf4 gene, a c-Myc gene, an hTERT gene, an SV40 Large T antigen (hereinafter, SV40LT) gene;

(5) an Oct3/4 gene, a Sox2 gene, a Klf4 gene, a c-Myc gene, an hTERT gene, an HPV16 E6 gene;

(6) an Oct3/4 gene, a Sox2 gene, a Klf4 gene, a c-Myc gene, an hTERT gene, an HPV16 E7 gene;

(7) an Oct3/4 gene, a Sox2 gene, a Klf4 gene, a c-Myc gene, an hTERT gene, an HPV6 E6 gene, an HPV16 E7 gene;

(8) an Oct3/4 gene, a Sox2 gene, a Klf4 gene, a c-Myc gene, an hTERT gene, a Bmil gene, (For the combinations (1) to (8), see WO2007/069666 (however, for the substitution from the Sox2 gene to the Sox18 gene and the substitution from the Klf4 gene to the Klf1 gene or the Klf5 gene in the combination (2), see Nature Biotechnology, 26, 101-106 (2008)). For the combination of "an Oct3/4 gene, a Sox2 gene, a Klf4 gene, a c-Myc gene", see also Cell, 126, 663-676 (2006), Cell, 131, 861-872 (2007), and the like. For the combination of "an Oct3/4 gene, a Sox2 gene, a Klf2 (or Klf5) gene, a c-Myc gene", see also Nat. Cell Biol., 11, 197-203 (2009). For the combination of "an Oct3/4 gene, a Sox2 gene, a Klf4 gene, a c-Myc gene, an hTERT gene, an SV40LT gene", see also Nature, 451, 141-146 (2008).)

(9) an Oct3/4 gene, a Sox2 gene, a Klf4 gene (see Nature Biotechnology, 26, 101-106 (2008));

(10) an Oct3/4 gene, a Sox2 gene, a Nanog gene, a Lin28 gene (see Science, 318, 1917-1920 (2007));

(11) an Oct3/4 gene, a Sox2 gene, a Nanog gene, a Lin28 gene, an hTERT gene, an SV40LT gene (see Stem Cells, 26, 1998-2005 (2008));

(12) an Oct3/4 gene, a Sox2 gene, a Klf4 gene, a c-Myc gene, a Nanog gene, a Lin28 gene (see Cell Research (2008) 600-603);

(13) an Oct3/4 gene, a Sox2 gene, a Klf4 gene, a c-Myc gene, an SV40LT gene (see Stem Cells, 26, 1998-2005 (2008));

(14) an Oct3/4 gene, a Klf4 gene (see Nature 454: 646-650 (2008), Cell Stem Cell, 2: 525-528 (2008));

(15) an Oct3/4 gene, a c-Myc gene (see Nature 454: 646-650 (2008));

(16) an Oct3/4 gene, a Sox2 gene (see Nature, 451, 141-146 (2008), WO2008/118820);

(17) an Oct3/4 gene, a Sox2 gene, a Nanog gene (see WO2008/118820);

(18) an Oct3/4 gene, a Sox2 gene, a Lin28 gene (see WO2008/118820);

(19) an Oct3/4 gene, a Sox2 gene, a c-Myc gene, an Esrrb gene (wherein the Essrrb gene is replaceable with an Esrrg gene. See Nat. Cell Biol., 11, 197-203 (2009));

(20) an Oct3/4 gene, a Sox2 gene, an Esrrb gene (see Nat. Cell Biol., 11, 197-203 (2009));

(21) an Oct3/4 gene, a Klf4 gene, an L-Myc gene;

(22) an Oct3/4 gene, a Nanog gene;

(23) an Oct3/4 gene;

(24) an Oct3/4 gene, a Klf4 gene, a c-Myc gene, a Sox2 gene, a Nanog gene, a Lin28 gene, an SV40LT gene (see Science, 324: 797-801 (2009));

In the combinations (1) to (24), other member genes of Oct gene family (for example, Oct1A, Oct6) may be used instead of an Oct3/4 gene. Moreover, other member genes of Sox gene family (for example, a Sox7 gene) can be used instead of a Sox2 gene (or a Sox1 gene, a Sox3 gene, a Sox15 gene, a Sox17 gene, a Sox18 gene). Furthermore, other member genes of Lin gene family (for example, a Lin28b gene) can be used instead of a Lin28 gene.

Moreover, a combination that is not the same as any of the combinations (1) to (24), but includes all components in any one of the (1) to (24) and further includes any other substance (preferably another nuclear reprogramming substance) can be included in the category of "nuclear reprogramming substance" in the present invention. Moreover, under conditions in which somatic cells to be nuclear-reprogrammed endogenously expresses a part of the components in any of the combinations (1) to (24) at a level sufficient for the nuclear reprogramming, combinations of the remaining components except the expressed components may also be included in the category of "nuclear reprogramming substance" in the present invention.

Furthermore, in addition to the nuclear reprogramming substances, one or more nuclear reprogramming substances selected from the group consisting of an Fbx15 gene, an ERas gene, an ECAT15-2 gene, a Tcl1 gene, and a β-catenin gene may be combined and/or one or more nuclear reprogramming substances selected from the group consisting of an ECAT1 gene, an Esg1 gene, a Dnmt3L gene, an ECAT8 gene, a Gdf3 gene, a Mybl2 gene, an ECAT15-1 gene, an Fthl17 gene, a Sall4 gene, a Rex1 gene, a UTF1 gene, a Stella gene, a Stat3 gene, and a Grb2 gene may be combined. These combinations are specifically described in WO2007/69666.

Examples of preferable nuclear reprogramming substances include an Oct3/4 gene, a Sox2 gene, a Klf4 gene, a c-Myc gene (or an L-Myc gene), a Lin28 gene, and a Nanog gene and at least 1, preferably 2 or more, more preferably 3 or more selected from the group consisting of gene products thereof. Examples of particularly preferable combinations of nuclear reprogramming substances include: (1) an Oct3/4 gene or a gene product thereof, a Sox2 gene or a gene product thereof, and a Klf4 gene or a gene product thereof; (2) an Oct3/4 gene or a gene product thereof, a Sox2 gene or a gene product thereof, a Klf4 gene or a gene product thereof, and a c-Myc gene or a gene product thereof; and (3) an Oct3/4 gene or a gene product thereof, a Sox2 gene or a gene product thereof, a Klf4 gene or a gene product thereof, and an L-Myc gene or a gene product thereof; in particular, preferable examples include combinations of an Oct3/4 gene or a gene product thereof, a Sox2 gene or a gene product thereof, and a Klf4 gene or a gene product thereof; and combinations of an Oct3/4 gene or a gene product thereof, a Sox2 gene or a gene product thereof, a Klf4 gene or a gene product thereof, and an L-Myc gene or a gene product thereof; and in particular, preferable examples include a combination of an Oct3/4 gene, a Sox2 gene, and a Klf4 gene; and a combination of an Oct3/4 gene, a Sox2 gene, a Klf4 gene, and an L-Myc gene.

A c-Myc gene or a gene product thereof may be used as one of the nuclear reprogramming substances used in the present invention, but it is preferable not to use a c-Myc gene or a gene product thereof. This is because c-Myc is reported to reduce the percentage of Nanog-GFP-positive colonies and increase the carcinogenicity of cells (Nakagawa, M., et al., Generation of induced pluripotent stem cells without Myc from mouse and human fibroblasts. Nature biotechnology 26, 101-106 (2008)).

When the nuclear reprogramming substance is a gene or a gene product thereof, the source of such a gene is not particularly limited, but it may be selected as appropriate depending on the purpose and examples thereof include any mammal such as a human, a mouse, a rat, a cow, a sheep, a horse, and a monkey.

The sequence information of mouse and human cDNAs of the nuclear reprogramming substances can be obtained under GenBank accession numbers described in WO2007/069666. The Nanog gene is described under the name "ECAT4" in the pamphlet. Moreover, the sequence information of mouse and human cDNAs of the particularly preferable 3 genes (the Oct3/4 gene, the Sox2 gene, the Klf4 gene) among the nuclear reprogramming substances is also described below.

| Gene name | Mouse | Human |
|---|---|---|
| Oct3/4 | NM_013633 | NM_002701 |
| Sox2 | NM_011443 | NM_003106 |
| Klf4 | NM_010637 | NM_004235 |
| L-Myc | NM_008506 | NM_001033081 |

The cDNA sequence of the human Oct3/4 gene is set forth in SEQ ID No: 47, the amino acid sequence of the human Oct3/4 protein is set forth in SEQ ID No: 48, the cDNA sequence of the human Sox2 gene is set forth in SEQ ID No: 49, the amino acid sequence of the human Sox2 protein is set forth in SEQ ID No: 50, the cDNA sequence of the human Klf4 gene is set forth in SEQ ID No: 51, the amino acid sequence of the human Klf4 protein is set forth in SEQ ID No: 52, the cDNA sequence of the human L-Myc gene is set forth in SEQ ID No: 53, and the amino acid sequence of the human L-Myc protein is set forth in SEQ ID No: 54.

Among the nuclear reprogramming substances, sequence information of mouse and human cDNAs of the genes whose GenBank accession numbers are not described in WO2007/069666 is described below.

| Gene name | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

Those skilled in the art can easily isolate cDNAs of these nuclear reprogramming substances based on the sequence information of mouse and human cDNAs of the nuclear reprogramming substances.

When the nuclear reprogramming substances are the genes or the mRNAs thereof, the nucleotide sequences thereof are not particularly limited as long as the effect of the present invention is unimpaired and they may be only the part translated into protein in the nucleotide sequences of the genes or contain other parts. Moreover, the nucleotide sequences of the genes and the nucleotide sequences of the mRNAs thereof may be the same as the nucleotide sequences of the wild-type genes or the nucleotide sequences of the mRNAs thereof or may comprise a mutation. Examples of such a nucleotide sequence comprising a mutation include a "nucleotide sequence that is modified from the nucleotide sequence of the wild-type gene or the nucleotide sequence of the mRNA thereof by a deletion, a substitution, an insertion, or an addition of 1 to 30, preferably 1 to 20, more preferably 1 to 15, more preferably 1 to 10, more preferably 1 to 5, more preferably 1 to 3 nucleotides and encodes a protein having the nuclear reprogramming effect of the gene product of the gene" and a "nucleotide sequence that has 70% or more, preferably 80% or more, more preferably 85% or more, more preferably 90% or more, more preferably 95% or more, more preferably 98% or more sequence identity with the nucleotide sequence of the wild-type gene or the nucleotide sequence of the mRNA thereof in the nucleotide sequence in the part to be translated into protein and encodes a protein having the nuclear reprogramming effect of the gene product of the gene".

When the nuclear reprogramming substances are the proteins encoded by the genes (that is, the proteins translated from the mRNAs transcribed from the genes), the amino acid sequences thereof may be the same as those of the proteins encoded by the wild-type genes or may comprise a mutation. Examples of such a protein comprising a mutation include a "protein that consists of an amino acid sequence modified from the amino acid sequence of the protein encoded by the wild-type gene by a deletion, a substitution, an insertion, or an addition of 1 to 30, preferably 1 to 20, more preferably 1 to 15, more preferably 1 to 10, more preferably 1 to 5, more preferably 1 to 3 amino acids and has the nuclear reprogramming effect" and a "protein that consists of an amino acid sequence having 70% or more, preferably 80% or more, more preferably 85% or more, more preferably 90% or more, more preferably 95% or more, more preferably 98% or more sequence identity with the amino acid sequence of the protein that the wild-type gene encodes and has the nuclear reprogramming effect".
(Somatic Cell)

The somatic cell is not particularly limited, but may be selected as appropriate depending on the purpose and examples thereof include a fetal somatic cell and a mature somatic cell. Specific examples of the mature somatic cell include a tissue stem cell (somatic stem cell) such as a mesenchymal stem cell, a hematopoietic stem cell, an adipose-derived stromal cell, an adipose-derived stromal stem cell, a neural stem cell, and a spermatogenic stem cell; a tissue progenitor cell, a differentiated cell such as a fibroblast, an epithelial cell, a lymphocyte, and a muscle cell.

The species of organism from which the somatic cell is derived is not particularly limited, but may be selected as appropriate depending on the purpose and examples thereof include any mammal such as a human, a mouse, a rat, a cow, a sheep, a horse, and a monkey. Moreover, the species of organism from which the somatic cell is derived and the species of organism from which the gene to be introduced into the somatic cell derived do not need to be the same, but they are preferably the same.

The individual from which the somatic cell is harvested is not particularly limited, but may be selected as appropriate depending on the purpose and when obtained iPS cells are to be used for the regenerative medical use, the individual to be treated or another individual having the same or a substantially same MHC type is preferable from the viewpoint of the rejection. The substantially same MHC type refers to an MHC type that matches to the degree that allows the engraftment of the transplanted cells by the use of an immunosuppressive drug or the like when the cells obtained by inducing differentiation from the iPS cells derived from the somatic cell are transplanted into the individual.

The somatic cell may be recombinant to facilitate the selection of an iPS cell. Specific examples of the recombinant somatic cell include a recombinant somatic cell in which at least either of a reporter gene and a drug resistance gene incorporated at the locus of the gene that is highly expressed specifically in pluripotent cells. Examples of the gene that is highly expressed specifically in pluripotent cells include an Fbx15 gene, a Nanog gene, and an Oct3/4 gene. Examples of the reporter gene include a green fluorescent protein (GFP) gene, a luciferase gene, and a beta-galactosidase gene. Examples of the drug resistance gene include a blasticidin gene, a hygromycin gene, a puromycin resistance gene, and a neomycin resistance gene.

Culture conditions for the somatic cell are not particularly limited, but may be selected as appropriate depending on the purpose and examples thereof include a culture temperature of approximately 37° C. and a $CO_2$ concentration of approximately 2% to 5%. The medium to be used for culturing the somatic cells is not particularly limited, but may be selected as appropriate depending on the purpose and examples thereof include a minimum essential medium (MEM), Dulbecco's modified Eagle medium (DMEM), RPMI1640 medium, 199 medium, F12 medium containing 5% by mass to 20% by mass serum.
(Method for Introducing (a) Nuclear Reprogramming Substance and (b) H1foo Gene or Gene Product Thereof into a Somatic Cell)

The method for introducing (a) a nuclear reprogramming substance and (b) an H1foo gene or a gene product thereof into a somatic cell is not particularly limited, but may be selected as appropriate depending on the purpose and examples thereof include a method involving use of an expression vector, a method involving use of mRNA, and a method involving use of a recombinant protein. In consideration of ease of the introduction into the somatic cell, it is more preferable that the nuclear reprogramming substance is introduced into the somatic cell in the form of a gene or in the form of mRNA of the gene rather than in the form of protein and it is more preferable that it is introduced into the somatic cell in the form of a gene. Such a gene may be DNA or RNA or it may be a DNA/RNA chimera, but it is preferable to be DNA from the viewpoint of stability. The gene may be double-stranded or single-stranded, but it is preferable to be double-stranded. Examples of the preferable nuclear reprogramming substance include cDNA of the gene and, in particular, preferably include a double-stranded cDNA of the gene.

Similarly, in consideration of ease of the introduction into the somatic cell, it is more preferable that the "H1foo gene or gene product thereof" is introduced into the somatic cell in the form of a gene or in the form of mRNA of the gene rather than in the form of protein and it is more preferable that it is introduced into the somatic cell in the form of a gene. Such an H1foo gene may be DNA or RNA, or it may be a DNA/RNA chimera, but it is preferable to be DNA from the viewpoint of stability. The H1foo gene may be double-stranded or single-stranded, but it is preferable to be double-stranded. Preferable aspects of the "H1foo gene or gene product thereof" include the cDNA of the H1foo gene and, in particular, preferably include the double-stranded cDNA of the H1foo gene.
(Expression Vector)

When the nuclear reprogramming substance is introduced into the somatic cell in the form of a gene or when the H1foo gene is introduced into the somatic cell, the expression vector obtained by incorporating the nuclear reprogramming substance or H1foo gene in a suitable expression vector containing a promoter that can function in the somatic cell to be a host may be used preferably. The expression vector in which the nuclear reprogramming substance or H1foo gene is to be incorporated is not particularly limited, but may be selected as appropriate depending on the purpose and examples thereof include an episomal vector, an artificial chromosome vector, a plasmid vector, and a virus vector.

Examples of the promoter used in the expression vector include an SR α promoter, an SV40 early promoter, a retroviral LTR, a CMV (cytomegalovirus) promoter, an RSV (Rous sarcoma virus) promoter, an HSV-TK (herpes simplex virus thymidinekinase) promoter, an EF1α promoter, a metallothionein promoter, and a heat shock promoter. Moreover, the enhancer of the IE gene of human CMV may be used with the promoter. As an example, the CAG promoter (containing a cytomegalovirus enhancer, a chicken β-actin promoter, and a poly A signal of the β-globin gene) may be used.

The expression vector may contain, if desired, an enhancer, a poly A addition signal, a marker gene, an origin of replication, and a gene encoding a protein that binds to an origin of replication and controls the reproduction, besides the promoter. The marker gene refers to a gene that enables sorting or selection of a cell by introducing the marker gene into the cell. Specific examples of the marker gene include a drug resistance gene, a fluorescent protein gene, a luminescent enzyme gene, and a chromogenic enzyme gene. These may be used singly or in combination of 2 or more. Specific examples of the drug resistance gene include a neomycin resistance gene, a tetracycline resistance gene, a kanamycin resistance gene, a zeocin resistance gene, and a hygromycin resistance gene. Specific examples of the fluorescent protein gene include a green fluorescent protein (GFP) gene, a yellow fluorescent protein (YFP) gene, and a red fluorescent protein (RFP) gene. Specific examples of the luminescent enzyme gene include a luciferase gene. Specific examples of the chromogenic enzyme gene include a β-galactosidase gene, a β-glucuronidase gene, and an alkaline phosphatase gene.

The episomal vector is a vector capable of autonomously replicating extrachromosomally. Specific means for using the episomal vector is disclosed in Yu et al., Science, 324, 797-801 (2009). In a particularly preferable embodiment of the present invention, an episomal vector in which loxP sequences are placed in the same direction in 5' and 3' of the vector elements necessary for the replication of the episomal vector may be used. Since episomal vectors are capable of autonomously replicating extrachromosomally, they can provide a stable expression in host cells without being incorporated into genome. However, it is desirable that the vector is removed promptly after an iPS cell is established. By having 2 loxP sequences flanking the vector elements necessary for the replication of the episomal vector and the recombinase Cre acting on it to cut the vector elements out, the autonomous replication competence of the episomal vector can be lost and the vector can be removed early from the iPS cell.

Examples of the episomal vector used in the present invention include a vector containing sequences necessary for the autonomous replication derived from EBV, SV40, or the like as the vector elements. The vector elements necessary for the autonomous replication are specifically an origin of replication and a gene encoding a protein that binds to the origin of replication and controls the replication and examples thereof include the origin of replication oriP and the EBNA-1 gene in EBV and the origin of replication ori and the SV40LT gene in SV40.

Moreover, examples of the artificial chromosome vector include a yeast artificial chromosome (YAC) vector, a bacterial artificial chromosome (BAC) vector, and a P1-derived artificial chromosome (PAC) vector.

Moreover, the plasmid vector is not particularly limited as long as it is a plasmid vector that can be expressed in the somatic cell into which it is to be introduced and examples thereof include a plasmid vector for expression in animal cells, such as pA1-11, pXT1, pRc/CMV, pRc/RSV, and pcDNAI/Neo, when the somatic cell is of a mammal.

Examples of the virus vector include a retrovirus (including lentivirus) vector, an adenovirus vectors, an adeno-associated virus vector, a Sendai virus vector, a herpes virus vector, a vaccinia virus vector, a pox virus vector, a poliovirus vector, a Sindbis virus vector, a rhabdovirus vector, a paramyxovirus vector, and an orthomyxovirus vector.

The method for introducing the expression vector into the somatic cell is not particularly limited, but may be selected as appropriate depending on the purpose and examples thereof include the lipofection, the microinjection, a DEAE dextran method, a gene gun method, the electroporation, and a calcium phosphate method.

When a virus vector is used as the expression vector for the introduction into the somatic cell, viral particles obtained by using a packaging cell may be used. Such a packaging cell is a cell in which the genes encoding the structural proteins of the virus are introduced and that, when a recombinant virus vector having a target gene incorporated therein is introduced in the cell, produces recombinant viral particles in which the target gene is incorporated. The packaging cell is not particularly limited, but may be selected as appropriate depending on the purpose and examples thereof include a packaging cell based on an HEK293 cell derived from a human kidney and an NIH3T3 cell derived from a mouse fibroblast, a PLAT-E cell, which is designed to express the envelope glycoproteins derived from Ecotropic virus, a PLAT-A cell, which is designed to express the envelope glycoproteins derived from Amphotropic virus, and a PLAT-GP cell, which is designed to express the envelope glycoproteins derived from vesicular stomatitis virus. In particular, the PLAT-A cell and the PLAT-GP cell are preferable in terms of the host tropism when a recombinant virus vector is introduced into the human somatic cell. The method for introducing the virus vector into the packaging cell is not particularly limited, but may be selected as appropriate depending on the purpose and examples thereof include the lipofection, the electroporation, and a calcium phosphate method. The method for infecting the somatic cell with the obtained viral particles is not particularly limited, but may be selected as appropriate depending on the purpose and examples thereof include a polybrene method.

When the nuclear reprogramming substance or the H1foo gene is introduced into the somatic cell using the expression vector, one gene or 2 or more genes may be incorporated into one expression vector. The incorporation of 2 or more genes in one vector enables simultaneous expression (which may hereinafter be referred to as "co-expression") of the 2 or more genes. Moreover, all nuclear reprogramming substances to be introduced into the somatic cell and an H1foo gene may be incorporated into one expression vector.

The method for incorporating the 2 or more genes into the one vector is not particularly limited, but may be selected as appropriate depending on the purpose, but it is preferable to incorporate the 2 or more genes with a linker sequence. Such a linker sequence is not particularly limited, but may be selected as appropriate depending on the purpose and examples thereof include a gene sequence encoding a 2A peptide derived from foot-and-mouth disease virus (*Picornaviridae Aphthovirus*) and an internal ribosome entry site (IRES).

The method for producing an iPS cell according to the present invention may involve introducing (a) a nuclear reprogramming substance and (b) a gene product of an H1foo gene in the form of mRNA into a somatic cell. The method for introducing the mRNA (messenger RNA) into the somatic cell is not particularly limited and a known method may be selected and used as appropriate. For example, a commercially available RNA transfection reagent such as Lipofectamine® MessengerMAX (manufactured by Life Technologies Corporation) or the like may be used.

The method for producing an iPS cell according to the present invention may involve introducing (a) a nuclear reprogramming substance and (b) a gene product of an H1foo gene in the form of protein into a somatic cell. The method for introducing such a protein into the somatic cell is not particularly limited and a known method may be selected and used as appropriate. Examples of such a method include a method involving use of a protein transfection reagent, a method involving use of a protein transduction domain (PTD)-fusion protein, and the microinjection. Commercially available protein transfection reagents include the cationic lipid-based reagents BioPOTER® Protein Delivery Reagent (manufactured by Gene Therapy Systems, Inc.) and Pro-Ject™ Protein Transfection Reagent (manufactured by PIERCE), the lipid-based reagent Profect-1 (manufactured by Targeting Systems), the membrane permeable peptide-based reagents Penetratin Peptide (manufactured by Q biogene Inc.) and Chariot Kit (manufactured by Active Motif), and GenomONE (manufactured by Ishihara Sangyo Kaisha, Ltd.), which uses an HVJ envelope (inactivated Sendai virus). The introduction may be conducted according to protocols attached to these reagents, but a common procedure is as follows. "(a) A nuclear reprogramming substance" and/or "(b) an H1foo gene or a gene product thereof" that are in the form of protein are diluted in a suitable solvent (for example, a buffer solution such as PBS or HEPES) and incubated at room temperature for about 5 to 15 minutes after the addition of a transfection reagent to form a complex. This is added to cells that have been transferred to a serum-free medium and the resultant culture may be incubated at 37° C. for from 1 hour to several hours. The medium may be removed subsequently and replaced to a serum-containing medium.

Examples of the PTD include that developed by using a cell penetrating domain of a protein such as AntP derived from *Drosophila*, TAT derived from HIV, or VP22 derived from HSV. Such a PTD may be used for introduction by constructing a fusion protein-expression vector in which cDNA of "(a) a nuclear reprogramming substance" and/or "(b) a gene product of an H1foo gene" and the PTD sequence is incorporated, recombinantly expressing these, and collecting the fusion protein. The introduction of such a fusion protein may be conducted as described above except that the protein transfection reagent is not added.

The microinjection is a method involving placing a protein solution in a glass needle having a tip diameter of about 1 μm and puncturing a cell to introduce the solution into the cell and enables reliable introduction of the protein into the cell. Methods for establishing iPS cells by introducing a nuclear reprogramming substance in the form of protein with a cell penetrating peptide (CPP) such as polyarginine or TAT has been developed in mouse and in human and these techniques may be used (Cell Stem Cell, 4: 381-384 (2009)).

In the method for producing an iPS cell according to the present invention, the introduction of "(a) a nuclear reprogramming substance" and "(b) an H1foo gene or a gene product thereof" into a somatic cell may be once or two or more times. The timing of introduction is not particularly limited, but may be selected as appropriate depending on the purpose and "(a) a nuclear reprogramming substance" and "(b) an H1foo gene or a gene product thereof" to be introduced may all be introduced in the same period of time or a part or all of them may be introduced at a different period(s) of time. The "H1foo gene or gene product thereof" may be an aspect in which only the gene is used, an aspect in which only the gene product thereof is used, or an aspect in which both of the gene and the gene product thereof are used. When the nuclear reprogramming substance is a gene or a gene product thereof, it may be an aspect in which only the gene is used, an aspect in which only the gene product thereof is used, or an aspect in which both of the gene and the gene product thereof are used. Moreover, the nuclear reprogramming substance is a gene(s) or a gene product(s) thereof and 2 or more "genes or gene products thereof" are used in combination, it may be an aspect in which as to a certain gene(s) the gene product(s) is used and as to the other gene(s) the gene(s) is used.

The amount of introduction of an H1foo gene or a gene product thereof into a somatic cell is not particularly limited as long as higher-quality iPS cells with smaller variance in quality can be produced when (a) a nuclear reprogramming substance and (b) the H1foo gene or gene product thereof are introduced into the somatic cell. Moreover, when the nuclear reprogramming substance is a gene(s) or a gene product(s) thereof, the amount(s) of introduction of the gene(s) or gene product(s) thereof into a somatic cell is not particularly limited as long as the nucleus of such a somatic cell can be reprogrammed and all gene(s) or gene product(s) thereof to be used may be introduced at the same amount or they may be introduced at different amounts. In an example in which the gene or gene product thereof which is used is a gene, an Oct3/4 gene is preferably introduced at a large amount, for example at approximately 3 times amount, relative to a Sox2 gene, a Klf4 gene, or a c-Myc gene (PNAS 106 (31): 12759-12764 (2009); J. Biol. Chem. 287(43): 36273-36282 (2012)).

When the nuclear reprogramming substance to be used in the method for producing an iPS cell according to the present invention is a low molecular weight compound, such a low molecular weight compound may be brought into contact with the somatic cell by dissolving the low molecular weight compound into an aqueous or non-aqueous solvent at an appropriate concentration, adding the solution of the low molecular weight compound into a medium suitable for the culture of the somatic cell (for example, a minimum essential medium (MEM), Dulbecco modified Eagle medium (DMEM), RPMI1640 medium, 199 medium, F12 medium containing approximately 5 to 20% of fetal bovine serum) so that the concentration of the low molecular weight compound is sufficient to cause the nuclear reprogramming in the somatic cell and in the range in which the cytotoxicity is not found, and culturing the cell for a certain period of time. The concentration of the low molecular weight compound that is the nuclear reprogramming substance depends on the kind of the low molecular weight compound to be used, but it may be selected as appropriate in a range of about 0.1 nM to about 100 nM. The duration of the contact is not particularly limited as long as it is a period of time that is long enough to cause the nuclear reprogramming of the cell, but they may usually be left together in the medium until a positive colony appears.

<Other Step>

As described above, the method for producing an iPS cell according to the present invention comprises at least the step of introducing (a) a nuclear reprogramming substance and (b) an H1foo gene or a gene product thereof into a somatic cell ("introduction step") and may further comprise another step(s) as needed. The other step(s) is not particularly limited as long as the effect of the present invention is unimpaired, but may be selected as appropriate depending on the purpose and examples thereof include a step of culturing the somatic cell in which (a) the nuclear reprogramming substance and (b) the H1foo gene or gene product thereof are introduced (hereinafter also referred to simply as "transfected cell".) (hereinafter also referred to simply as "transfected cell-culturing step".).

(Transfected Cell-culturing Step)

The transfected cell-culturing step is a step of culturing a somatic cell in which (a) the nuclear reprogramming substance and (b) the H1foo gene or gene product thereof are introduced. The culture conditions for the transfected cell are not particularly limited and examples thereof include conditions suitable for culturing ES cells. Examples of such conditions include a culture temperature of approximately 37° C. and a $CO_2$ concentration of approximately 2% to 5%. Moreover, the medium to be used for culturing the transfected cell is not particularly limited, but may be selected as appropriate depending on the purpose. Mouse cells are cultured in a normal medium to which Leukemia Inhibitory Factor (LIF) is added as a differential inhibitory factor. For human cells, basic fibroblast growth factor (bFGF) and/or stem cell factor (SCF) is desirable to be added instead of LIF. Moreover, cells are usually cultured in the presence of mouse embryonic fibroblasts (MEFs) treated with a radiation or an antibiotic to be arrested in cell division, as feeder cells. As MEFs, STO cells are usually used often, but SNL cells (McMahon, A. P. & Bradley, A. Cell 62, 1073-1085 (1990)) or the like are used often for the induction of iPS cells. The co-culture with feeder cells may be started prior to the introduction of (a) a nuclear reprogramming substance and (b) an H1foo gene or a gene product thereof, at the time of the introduction, or after the introduction (for example, 1 to 10 days later).

The duration of the transfected cell-culturing step is not particularly limited, but may be selected as appropriate depending on the purpose.

2. iPS Cell

The iPS cell according to the present invention prepared by the method for producing an iPS cell has the pluripotency and the self-renewal capacity. The pluripotency means the ability to differentiate into all three germ-layer lineages. The self-renewal capacity means the ability to replicate while maintaining an undifferentiated state.

The method for confirming that the cell produced by the method for producing an iPS cell is an iPS cell is not particularly limited, but may be selected as appropriate depending on the purpose. For example, when the cell used as the somatic cell is a recombinant somatic cell in which at least either of a reporter gene and a drug resistance gene is incorporated at the locus of the gene highly expressed specifically in pluripotent cells (for example, Fbx15, Nanog, or Oct3/4, preferably Nanog or Oct3/4), the confirmation can be made using the reporter gene or drug resistance gene. Specific examples when the gene used as the reporter gene is a green fluorescent protein (GFP) gene include a method involving confirming a GFP-positive cell with a flow cytometer and, when the gene used as the drug resistance gene is a puromycin resistance gene, the confirmation can be made by adding puromycin to the cell.

As used herein, the term "high-quality iPS cells" means iPS cells whose quality is higher than iPS cells produced in the same way except that neither H1foo gene nor gene product thereof is introduced into the somatic cell. Moreover, as used herein, the term "iPS cells with smaller variance in quality" means iPS cells that have variance in quality smaller than that of iPS cells produced in the same way except that neither H1foo gene nor gene product thereof is introduced into the somatic cell. The quality in these may be of one kind or of 2 or more kinds. Specific examples of the "high-quality iPS cells" or the "iPS cells with smaller variance in quality" include iPS cells having one or more properties selected from the following (a) to (q).

(a) iPS cells that form embryoid bodies increased in number by 5% or more or preferably 10% or more in comparison with iPS cells (preferably "OSK-iPS cells" or "OSKL-iPS cells" in Examples described below) produced in the same way except that neither H1foo gene nor gene product thereof is introduced into the somatic cell when cultured for 5 days by a method of [Embryoid body (EB) formation] described below.

(b) iPS cells that form 78 or more or preferably 80 or more embryoid bodies when cultured for 5 days by a method of [Embryoid body (EB) formation] described below.

(c) iPS cells that form embryoid bodies with size ($\mu m^2$) variance ($\sigma^2$) decreased by 25% or more or preferably 40% or more in comparison with iPS cells (preferably "OSK-iPS cells" or "OSKL-iPS cells" in Examples described below) produced in the same way except that neither H1foo gene nor gene product thereof is introduced into the somatic cell when cultured for 5 days by a method of [Embryoid body (EB) formation] described below.

(d) iPS cells that form embryoid bodies with size ($\mu m^2$) variance ($\sigma^2$) of 10000 ($\mu m^2$) or less or preferably 8000 ($\mu m^2$) or less when cultured for 5 days by a method of [Embryoid body (EB) formation] described below.

(e) iPS cells in which the percentage of viable cells (annexin V (−)/PI (−) cells) as measured by a method of [Apoptosis assay] described below is increased to 1.1 times or more or preferably 1.2 times or more in comparison with iPS cells (preferably "OSK-iPS cells" or "OSKL-iPS cells" in Examples described below) produced in the same way except that neither H1foo gene nor gene product thereof is introduced into the somatic cell.

(f) iPS cells in which the percentage of viable cells (annexin V (−)/PI (−) cells) as measured by a method of [Apoptosis assay] described below is 68% or more or preferably 73% or more.

(g) iPS cells in which the percentage of apoptotic cells (the sum of annexin V (+)/PI (−) cells and annexin V (+)/PI (+) cells) as measured by a method of [Apoptosis assay] described below is decreased to 0.75 times or less or preferably 0.67 times or less in comparison with iPS cells (preferably "OSK-iPS cells" or "OSKL-iPS cells" in Examples described below) produced in the same way except that neither H1foo gene nor gene product thereof is introduced into the somatic cell.

(h) iPS cells in which the percentage of apoptotic cells (the sum of annexin V (+)/PI (−) cells and annexin V (+)/PI (+) cells) as measured by a method of [Apoptosis assay] described below is 30% or less or preferably 25% or less.

(i) iPS cells in which the expression level of the Ki67 gene or the PCNA gene (both genes are known as a cell proliferation marker) as measured by the method described in the section of [Quantitative RT-PCR analysis] below is increased to 1.7 times or preferably 2.2 times in comparison with iPS cells (preferably "OSK-iPS cells" or "OSKL-iPS cells" in Examples described below) produced in the same way except that neither H1foo gene nor gene product thereof is introduced into the somatic cell.

(j) iPS cells in which the expression level of the Ki67 gene or the PCNA gene (both genes are known as a cell proliferation marker) as measured by the method described in the section of [Quantitative RT-PCR analysis] described below is 0.65 times or more or preferably 0.73 times or more of that of ES cells.

(k) iPS cells with higher chimera competency in comparison with iPS cells (preferably "OSK-iPS cells" or "OSKL-iPS cells" in Examples described below) produced in the same way except that neither H1foo gene nor gene product thereof is introduced into the somatic cell.

(l) iPS cells with higher germline transmission potential in comparison with iPS cells (preferably "OSK-iPS cells" or "OSKL-iPS cells" in Examples described below) produced in the same way except that neither H1foo gene nor gene product thereof is introduced into the somatic cell.

(m) iPS cells in which the expression level of the SRF gene (the SRF gene is known as a chromosomal abnormality marker whose expression level decreases when there is chromosomal abnormality) as measured by the method described in the section of [Quantitative RT-PCR analysis] described below is increased to 1.1 times or preferably 1.2 times in comparison with iPS cells (preferably "OSKL-iPS cells" or "OSK-iPS cells" in Examples described below) produced in the same way except that neither H1foo gene nor gene product thereof is introduced into the somatic cell.

(n) iPS cells in which the expression level of the ACTG2 gene (the ACTG2 gene is known as a chromosomal abnormality marker whose expression level decreases when there is chromosomal abnormality) as measured by the method described in the section of [Quantitative RT-PCR analysis] described below is increased to 1.2 times or preferably 1.5 times in comparison with iPS cells (preferably "OSKL-iPS cells" or "OSK-iPS cells" in Examples described below) produced in the same way except that neither H1foo gene nor gene product thereof is introduced into the somatic cell.

(o) iPS cells in which the variance ($\sigma^2$) of expression levels of the Oct3/4 gene (an undifferentiated state marker of stem cells) as measured by the method described in the section of [Quantitative RT-PCR analysis] described below is decreased by 10% or more or preferably 20% or more in comparison with iPS cells (preferably "OSKL-iPS cells" or "OSK-iPS cells" in Examples described below) produced in the same way except that neither H1foo gene nor gene product thereof is introduced into the somatic cell.

(p) iPS cells in which the number of viable cells as measured by the method described in the section of [Comparison of cell survival rates in early stage after induction of differentiation] described below is increased to 1.2 times or preferably 1.5 times in comparison with iPS cells (preferably "OSKL-iPS cells" or "OSK-iPS cells" in Examples described below) produced in the same way except that neither H1foo gene nor gene product thereof is introduced into the somatic cell.

(q) iPS cells in which the variance ($\sigma^2$) of expression levels of the Oct3/4 gene (an undifferentiated state marker of stem cells) as measured by the method described in the section of [Comparison of residual amounts of undifferentiated state marker in early period after induction of differentiation of iPS cells] described below is decreased by 10% or more or preferably 20% or more in comparison with iPS cells (preferably "OSKL-iPS cells" or "OSK-iPS cells" in Examples described below) produced in the same way except that neither H1foo gene nor gene product thereof is introduced into the somatic cell.

The species of organism from which the iPS cells are derived is not particularly limited, but may be selected as appropriate depending on the purpose and examples thereof include any mammal such as a human, a mouse, a rat, a cow, a sheep, a horse, and a monkey.

3. Agent for Improving Quality of an iPS Cell

The Agent for improving quality of an iPS cell according to the present invention comprises at least an H1foo gene or a gene product thereof and may further comprise another configuration as needed. The H1foo gene or gene product thereof is similar to the one described for the method for producing an iPS cell. Moreover, the H1foo gene or gene product thereof may comprise a similar mutation described for the method for producing an iPS cell. Moreover, the H1foo gene incorporated in the expression vector containing a promoter that can function in the somatic cell to be a host may be used.

4. Composition for Producing iPS Cell

The composition for producing an iPS cell according to the present invention comprises at least (a) a nuclear reprogramming substance and (b) H1foo gene or a gene product thereof and may further comprise another configuration as needed.

<(a) Nuclear Reprogramming Substance and (b) H1foo Gene or Gene Product Thereof>

The (a) nuclear reprogramming substance and (b) H1foo gene or gene product thereof are similar to those described for the method for producing an iPS cell. Moreover, the H1foo gene or gene product thereof and a gene or a gene product thereof that is the nuclear reprogramming substance may comprise a similar mutation described for the method for producing an iPS cell.

Examples of the preferable form of the nuclear reprogramming substance in the composition for producing an iPS cell include a form of a gene incorporated in a vector, a form of synthetic mRNA, and a form of protein (preferably recombinant protein). Examples of the vector include that similar to those described in the method for producing an iPS cell. The synthetic mRNA and the protein (preferably recombinant protein) may be produced by a known method.

The composition for producing an iPS cell may be packed such that the (a) nuclear reprogramming substance and the (b) H1foo gene or gene product thereof are contained separately in individual containers or together in one container or in group of any number per container in containers.

The amounts of the (a) nuclear reprogramming substance and the (b) H1foo gene or gene product thereof in the composition for producing an iPS cell are not particularly limited and all of the nuclear reprogramming substance(s) and/or the H1foo gene or gene product thereof may be contained in the same amount or in different amounts.

The composition for producing an iPS cell may comprise, besides the (a) nuclear reprogramming substance and the (b) H1foo gene or gene product thereof, a gene or a gene product thereof other than these. Moreover, when the virus vector is used, the composition may comprise, for example, a packaging cell. Examples of such a gene or a gene product thereof other than the genes or gene products thereof and such a packaging cell include those described for the method for producing an iPS cell.

The present invention also comprises, as other aspects, "a method for improving quality of an iPS cell, comprising the step of introducing an H1foo gene or a gene product thereof into a somatic cell", "use of an H1foo gene or a gene product thereof in the manufacture of an agent for improving quality of an iPS cell", and "use of (a) a nuclear reprogramming substance and (b) an H1foo gene or a gene product thereof in the manufacture of a composition for producing an iPS cell".

The step of introducing an H1foo gene or a gene product thereof into a somatic cell in the "method for improving quality of an iPS cell" is the same as the introduction step in the method for producing an iPS cell according to the present invention. Comprising such a step enables improving quality of an iPS cell and obtaining a high-quality iPS cell.

The present invention will be described by means of Examples below in detail, but the present invention is not limited to these Examples. All experiments described below were conducted according to the Guidelines on Animal and DNA Experimentation at Keio University, approved by the Ethical Committee at Keio University, and based on the Guide for the Care and Use of Laboratory Animals at the National Institute of Health.

EXAMPLES

1. Materials and Method
[Plasmid Construction]

H1foo cDNA and H1c cDNA (Teranishi, T., et al., Rapid replacement of somatic linker histones with the oocyte-specific linker histone H1foo in nuclear transfer. Developmental Biology 266, 76-86 (2004).) were inserted respectively into the restriction enzyme BamH1-Sal1 and EcoR1-

Sal1 sites in the pMXs plasmid and it was confirmed by DNA sequencing that the H1foo cDNA and the H1c cDNA were inserted.

[Production of Mouse iPS Cells and Method for Culturing the Same]

1) The production of mouse iPS cells was conducted following a protocol described in literature (Takahashi, K., Okita, K., Nakagawa, M., & Yamanaka, S. Induction of pluripotent stem cells from fibroblast cultures. Nature protocols 2, 3081-3089 (2007)). In this study, however, the H1foo gene was also used in addition to the genes described in the document. More specifically, iPS cells were produced from mouse fibroblasts or tail tip fibroblasts (hereinafter simply referred to as "Nanog-GFP expressing fibroblasts") in a Nanog-GFP-IRES-puro transgenic mouse (Okita, K., Ichisaka, T. & Yamanaka, S. Generation of germline-competent induced pluripotent stem cells. Nature 448, 313-317 (2007)) using the retrovirus vector pMXs containing mouse Oct3/4, Sox2, Klf4, and H1foo genes (nucleotide sequence set forth in SEQ ID No: 3: BC137916). As a control, DsRed gene was used instead of the H1foo gene. The management of laboratory mice was conducted following the Guidelines on Animal and DNA Experimentation at Keio University.

2) Mouse ES cells (B6J-23$^{UTR}$) (Tanimoto, Y., et al. Embryonic stem cells derived from C57BL/6J and C57BL/6N mice. Comparative medicine 58, 347-352 (2008)) were obtained from the Laboratory Animal Resource Center at the University of Tsukuba and used following the Guidelines on the Distribution and Utilization of Human Embryonic Stem Cells of Ministry of Education, Culture, Sports, Science and Technology of Japan.

3) Mouse iPS and ES cell lines were cultured and maintained on X-irradiated mouse embryonic fibroblasts (iMEF feeder cells) derived from a wild-type ICR mouse in DMEM (manufactured by Sigma Aldrich Co. LLC.) culture medium containing 20% KnockOut Serum Replacement (manufactured by Gibco), in 1 mM GlutaMAX (manufactured by Gibco), 1 mM nonessential amino acids (manufactured by Sigma Aldrich Co. LLC.), 0.1 mM 2-mercaptoethanol, 50 U penicillin, 50 mg/ml streptomycin (manufactured by Gibco), and mouse Leukemia Inhibitory Factor (LIF) (hereinafter referred to as "iPS cell culture medium"). The mouse iPS cell culture medium was replaced every 2 to 3 days and the cells were subcultured using 0.5 mM trypsin-EDTA (manufactured by Gibco) every 2 to 3 days.

[Embryoid Body (EB) Formation]

The EB formation from iPS cells was conducted by seeding 5×10$^4$ iPS cells obtained with 1 mg/ml collagenase IV on a 100 mm low attachment plate (manufactured by AGC Techno Glass Co. Ltd.) and culturing the cells for 5 days in the presence of Minimum Essential Medium Alpha Medium (manufactured by Gibco) containing 20% FBS (manufactured by Gibco), 2 mM GlutaMAX (manufactured by Gibco), 0.1 mM nonessential amino acids (manufactured by Sigma Aldrich Co. LLC.), 0.1 mM 2-mercaptoethanol, 50 U/ml penicillin, and 50 mg/ml streptomycin (manufactured by Gibco) (hereinafter referred to as "culture medium for EB formation"). The culture medium for EB formation was replaced every 2 to 3 days. As a control, ES cells were used.

[Teratoma Formation]

The teratoma-forming potential of the iPS cells were confirmed by hematoxylin eosin (HE) staining after injecting the iPS cells into the testis in SCID mice (manufactured by CLEA Japan, Inc.) anesthetized with a mixture of ketamine (50 mg/kg), xylazine (10 mg/kg), and chlorpromazine (1.25 mg/kg), sacrificing the mice by cervical vertebra dislocation approximately 8 weeks later, fixing the tissue sections in which iPS cells were injected in 10% paraformaldehyde (PFA) overnight and embedding the sections in paraffin. The anesthesia of mice was conducted appropriately by monitoring the heart rate, muscle relaxation, and sensual reflection response (that is, unresponsive to tail pinch) of the mice.

[Immunohistochemistry Staining]

The iPS cells and fibroblasts seeded on a glass bottom dish (product made in AGC Techno Glass Co. Ltd) were washed with PBS once and fixed with 4% paraformaldehyde (manufactured by Muto Pure Chemicals Co., Ltd.) at 4° C. for 15 minutes. Fixed cells were treated for permeabilization in 0.5% triton X-100 in PBS at room temperature for 10 minutes, then blocked in ImmunoBlock (manufactured by DS Pharma Biomedical Co. Ltd.) for 20 minutes, incubated in the presence of 4 primary antibodies (an anti-Oct3/4 antibody [Oct3/4 antibody sc-8629, manufactured by Santa Cruz Biotechnology, Inc.], an anti-Nanog antibody [RCAB0001P, manufactured by ReproCELL Inc.], an anti-SSEA1 antibody [sc-21702, manufactured by Santa Cruz Biotechnology, Inc.], and an anti-H1foo antibody [HPA037992, manufactured by Sigma Aldrich Co. LLC.]) at room temperature for 60 minutes, washed with ImmunoBlock (manufactured by DS Pharma Biomedical Co. Ltd.), and incubated with secondary antibodies (anti-rabbit IgG and anti-mouse IgG or IgM antibodies conjugated with Alexa Fluor 488 or Alexa Fluor 568 [manufactured by Life Technologies Corporation]) corresponding to the primary antibodies at room temperature for 60 minutes. After staining the nucleus with 6-diamidino-2-phenylindole (DAPI, manufactured by Life Technologies Corporation) the fluorescence observation was conducted using a fluorescence laser microscope equipped with a color charge-coupled device camera (BZ-9000, manufactured by Keyence Corporation), and an optical microscope (IX71, manufactured by Olympus Corporation), and a laser confocal microscope (LSM 510 META, manufactured by Carl Zeiss Jena GmbH).

[Quantitative RT-PCR Analysis]

Total RNA samples were isolated with a TRIZOL reagent (manufactured by Life Technologies Corporation) according to a manual attached to the product. The concentration and the purity of RNA samples were measured with an ND-1000 spectrophotometer (manufactured by Thermo Fisher Scientific Inc.) and the preparation of cDNA was performed using ReverTra Ace qPCR RT Master Mix (manufactured by Toyobo Co., Ltd.). Quantitative PCR (QT-PCR) was performed by 7500 Real Time PCR System (manufactured by Life Technologies Corporation) using SYBR Premix ExTaq (manufactured by Takara Bio Inc.). The amount of mRNA was normalized with amount of the GAPDH mRNA. The nucleotide sequences of the primer sets used for the quantitative PCR are set forth in Table 1 below.

TABLE 1

| Gene name | Forward primer | Reverse primer |
| --- | --- | --- |
| Nanog | AGGGTCTGCTACTGAGATGCT (SEQ ID No: 5) | CAACACCTGGTTTTTCTGCCACCG (SEQ ID No: 6) |

TABLE 1-continued

| Gene name | Forward primer | Reverse primer |
| --- | --- | --- |
| Oct3/4 (Endogenous) | TCTTTCCACCAGGCCCCCGGCTC (SEQ ID No: 7) | TGCGGGCGGACATGGGGAGATCC (SEQ ID No: 8) |
| Sox2 (Endogenous) | TAGAGATAGACTCCGGGCGATGA (SEQ ID No: 9) | TTGCCTTAAACAAGACCACGAAA (SEQ ID No: 10) |
| Oct3/4 (Transgene) | CCCCAGGGCCCCATTTTGGTACC (SEQ ID No: 11) | CCCTTTTTCTGGAGACTAATAAA (SEQ ID No: 12) |
| Sox2 (Transgene) | GGCACCCCTGGCATGGCTCTTGGCTC (SEQ ID No: 13) | TTATCGTCGACCACTGTGCTGCTG (SEQ ID No: 14) |
| Rex1 | ACGAGTGGCAGTTTCTTCTTGGGA (SEQ ID No: 15) | TATGACTCACTTCCAGGGGGCACT (SEQ ID No: 16) |
| Sall4 | CCCTGGGAACTGCGATGAAG (SEQ ID No: 17) | TCAGAGAGACTAAAGAACTCGGC (SEQ ID No: 18) |
| H1foo | GGCACAGGCTTTCTTTGTCT (SEQ ID No: 19) | TCCAACACAAGTACCCGACA (SEQ ID No: 20) |
| Foxa2 | AGCACCATTACGCCTTCAAC (SEQ ID No: 21) | CCTTGAGGTCCATTTTGTGG (SEQ ID No: 22) |
| Cxcr4 | CGGGATGAAAACGTCCATTT (SEQ ID No: 23) | ATGACCAGGATCACCAATCCA (SEQ ID No: 24) |
| Col6a2 | CCACCACTGAAAGGAACAACAA (SEQ ID No: 25) | TCCAACACGAAATACACGTTGAC (SEQ ID No: 26) |
| T | TGTCCTCCCTTGTTGCCTTA (SEQ ID No: 27) | ATGTTCCAAGGGCAGAACAG (SEQ ID No: 28) |
| β3-Tubulin | CCCAGCGGCAACTATGTAGG (SEQ ID No: 29) | CCAGACCGAACACTGTCCA (SEQ ID No: 30) |
| Tubb3 | CCAAATCTACCCACCAAGGA (SEQ ID No: 31) | AGAGCTTCCAGAACGTCGAG (SEQ ID No: 32) |
| Ki67 | TCTGATGTTAGGTGTTTGAG (SEQ ID No: 33) | CACTTTTCTGGTAACTTCTTG (SEQ ID No: 34) |
| PCNA | TAAAGAAGAGGAGGCGGTAA (SEQ ID No: 35) | TAAGTGTCCCATGTCAGCAA (SEQ ID No: 36) |
| GAPDH | TTCAACGGCACAGTCAAGG (SEQ ID No: 37) | CATGGACTGTGGTCATGAG (SEQ ID No: 38) |
| SRF | ACCCATAAGCCCCAGCTATC (SEQ ID No: 55) | GGTGCCAAGATGGAAGTCAC (SEQ ID No: 56) |
| ACTG2 | CGGTGGTCTCCTCTTCACAC (SEQ ID No: 57) | CACTGGGAGAAGAACCTCTCAT (SEQ ID No: 58) |

[Apoptosis Assay]

iPS cells at 1 day after the start of culturing in the culture medium for EB formation were trypsinized and suspended into Annexin A5 Binding Buffer (manufactured by Takara Bio Inc.) and then early apoptotic cells and late apoptotic cells were stained with annexin-A5-FITC and iodinated propidium (PI) (manufactured by Becton, Dickinson and Company), respectively, following the manual attached to the products. The cells were filtered through a nylon membrane with a pore size of 70 mm and the fluorescently stained cells were analyzed with the flow cytometry FACS Aria3 (manufactured by Becton, Dickinson and Company) using the software CellQuest (manufactured by Becton, Dickinson and Company) to determine the percentage of apoptotic cells using the software FlowJo (manufactured by Tree Star, Inc.).

[DNA Methylation Analysis]

To analyze the DNA methylation level in the promoter regions of the Oct3/4 and Nanog genes using bisulfite sequencing, genomic DNA was isolated and purified from cell samples using SV Genomic DNA Purification kit (manufactured by Promega Corporation). Unmethylated cytosine (C) in the purified genomic DNA was converted into uracil (U) using EZ DNA Methylation-Gold Kit (manufactured by ZYMO RESEARCH) following a manual attached to the product and input DNA for bisulfite PCR was prepared. Using such input DNA, primer sets, and TaKaRa EpiTaq HS (manufactured by TaKaRa Bio Inc.), bisulfite PCR was performed under the PCR reaction conditions (1 cycle of denaturing at 98° C. for 10 minutes; 40 cycles of amplification at 95° C. for 20 seconds, at 55° C. for 30 seconds, and at 72° C. for 60 seconds; and 1 cycle of the final extension at 72° C. for 5 minutes). The nucleotide sequences of the primer sets used for the bisulfite PCR are set forth in Table 2 below.

TABLE 2

| | | |
|---|---|---|
| Oct3/4-DMR | GGTTTTTTAGAGGATGGTTGAGTG (SEQ ID No: 39) | TCCAACCCTACTAACCCATCACC (SEQ ID No: 40) |
| Nanog-DMR | GATTTTGTAGGTGGGATTAATTGTGAATTT (SEQ ID No: 41) | ACCAAAAAAACCCACACTCATATCAATATA (SEQ ID No: 42) |

The PCR products were cloned into the vector pGEM-T (manufactured by Promega Corporation) by TA-cloning after purification and sequenced. To analyze the methylation status of the intergenic differentially methylated region (DMR) (IG-DMR) located between the Dlk1 and Dlk2 genes and the Gtl2 differentially methylated region (Gtl2-DMR), genomic DNA was purified as described above, input DNA for bisulfite PCR was prepared, and then pyrosequencing was conducted using PyroMark Q24 (manufactured by QIAGEN) following the manual attached to the product. The nucleotide sequences of primer sets used for the pyrosequencing are set forth in Table 3 below.

TABLE 3

| | | |
|---|---|---|
| IG-DMR | GTGGTTTGTTATGGGTAAGTTT (SEQ ID No: 43) | CCCTTCCCTCACTCCAAAAATTAA (SEQ ID No: 44) |
| Gt12-DMR | AGTTATTTTTGTTTGAAAGGATGTGTA (SEQ ID No: 45) | CTAACTTTAAAAAAAAATCCCCAACACT (SEQ ID No: 46) |

[Co-culture Aggregation of ES Cell and iPS Cell]

Embryos at the 2-cell stage were collected from superovulated and naturally mated female ICR (CD-1®) mice and then cultured to the blastocyst stage. ES cells and the iPS cells were dissociated with 0.25% trypsin just before co-culture aggregation and 15 to 20 cells were aggregated with blastomeres at the 8-cell stage from which the zonae pellucidae had been removed. Chimeric embryos at the blastocyst stage were transferred into the uterine horns of ICR pseudopregnant mice at 2.5 dpc (days of post-coitus).

[Global Gene Expression Analysis]

Total RNA was isolated from iPS cells and an ES cells. Cyanine-labeled antisense RNA was amplified using the Quick Amp Labeling Kit (manufactured by Agilent Technologies), hybridized onto a Whole Mouse Genome Oligo Microarray (manufactured by Agilent Technologies) with a gene expression hybridization kit, and analyzed with the Agilent Microarray Scanner. The data was analyzed with GeneSpring GX12.0 software (manufactured by Agilent Technologies).

[Statistical Analysis]

The values in bar graph with error bars in figures are reported as the mean±standard deviation (SME). The data was analyzed using StatView J-4.5 software. The comparison between 2 groups was performed with Student's t-test. The comparison among groups was performed by one-way ANOVA with Bonferroni's post hoc test. "*" and "**" in the figures indicate significance (P<0.05 and P<0.01, respectively).

2. Results

[Production of iPS Cells Using Exogenous H1foo Gene]

The effect of H1foo on somatic cell reprogramming was examined.

First, the method described in the section [Immunohistochemistry staining] above was conducted to confirm that exogenous H1foo is exclusively expressed in the nucleus (FIG. 1a) and that it is mostly located peripherally in the nucleus (FIG. 1b). Nuclear swelling and the decrease of the region having high electron density inside of the nuclear membrane (heterochromatin) by the expression of the exogenous H1foo were not observed (FIG. 1c).

Then, according to the method described in the section of [Production of murine iPS cells and method for culturing the same] above, 3 nuclear reprogramming substances (the Oct3/4, Sox2, and Klf4 genes [OSK genes]) as well as the H1foo gene (OSK+H1foo genes) were introduced into murine fibroblasts, which are somatic cells, using a retrovirus vector and alkaline phosphatase (ALP) staining was conducted using TRACP & ALP double-stain Kit (manufactured by Takara Bio Inc.) on Day 20 to determine the number of colonies that are ALP-positive and consist of ES-like cells. ALP is known as a stem cell marker. As control, experiments of introducing only the OSK genes or introducing the linker histone H1 gene (OSK+H1c genes) instead of H1foo in the OSK+H1foo genes were also conducted. As a result, it was shown that the introduction of OSK+H1foo genes into murine fibroblasts results in marked increase of the number of ALP-positive ES-like cell (iPS cell) colonies as compared with the introduction of the OSK genes or the OSK+H1c genes (FIG. 2a).

According to the method described in the section of [Immunohistochemistry staining] above, the expression of the 3 pluripotency markers (Oct3/4, Nanog, and SSEA1) was analyzed. The analysis demonstrated that the OSK+H1foo-iPS cells express the pluripotent markers as OSK-iPS cells do (FIG. 2b). In contrast, the expression of endogenous H1foo was observed neither during the induction process to iPS cells nor in the produced iPS cells (FIG. 2b, c).

Moreover, the OSK+H1foo genes were introduced into Nanog-GFP expressing fibroblasts to examine the quality of the produced iPS cells (FIG. 3a) using the signal of GFP as an indicator. The Nanog-GFP-positive cells are known as a marker for high-quality stem cells. Interestingly, it was shown that the introduction of the H1foo gene in addition to the OSK genes into Nanog-GFP expressing fibroblasts increases the number of colonies of Nanog-GFP-positive ES-like cells (iPS cells) to approximately 8 times as compared with the introduction of the OSK genes (FIG. 3b). Furthermore, the ratio of the Nanog-GFP-positive ES-like cells (iPS cells) to the produced iPS cell population was as high as 90% or more (FIG. 3c). In contrast, the introduction of the OSK genes and the c-Myc gene (OSKM genes) or the introduction of the H1foo gene as well as the OSKM genes (OSKM+H1foo genes) into Nanog-GFP expressing fibroblasts was shown to result in an increased number of Nanog-GFP-positive colonies themselves (FIG. 3b), but the ratio of Nanog-GFP-positive cells to the produced iPS cell population is low as compared with the introduction of the OSK+H1foo genes (FIG. 3c). These results indicate that the introduction of the OSK+H1foo genes into somatic cells enables the production of higher-quality iPS cell populations as compared with the introduction of the OSK genes or the introduction of the OSKM genes in the conventional art.

[Properties of OSK+H1foo-iPS Cells]

Properties of the OSK+H1foo-iPS cells were analyzed in detail. The analysis of the expression of 4 pluripotency markers (Oct3/4, Sox2, Rex1, and Sall4) according to the method described in the section of [Quantitative RT-PCR analysis] above demonstrated that the OSK+H1foo-iPS cells express the pluripotency markers as the OSK-iPS cells do (Table 4). The expression of the transgenes including the H1foo gene was suppressed (Table 5). The cell proliferation rate was also analyzed and the analysis indicated that the proliferation level of OSK+H1foo-iPS cells was equivalent to that of OSK-iPS cells.

TABLE 4

| Cell | Nanog | Oct3/4 | Sox2 | Rex1 | Sall4 |
|---|---|---|---|---|---|
| ES | 1.00 | 1.00 | 1.00 | 1.00 | 1.00 |
| OSK-iPS1 | 0.500 | 0.704 | 0.841 | 0.720 | 1.11 |
| OSK-iPS2 | 0.726 | 0.935 | 1.19 | 0.925 | 0.796 |
| OSK-iPS3 | 0.906 | 0.731 | 1.02 | 1.07 | 1.29 |
| OSKH-iPS1 | 0.764 | 0.796 | 1.39 | 0.897 | 0.548 |
| OSKH-iPS2 | 0.990 | 0.704 | 1.06 | 1.05 | 1.33 |
| OSKH-iPS3 | 0.689 | 0.917 | 1.22 | 0.869 | 0.903 |
| MEF | 0.00943 | 0.00 | 0.0341 | 0.00935 | 0.00 |

Table 4 shows the results of analysis of the expression of 5 pluripotency markers (Nanog, Oct3/4, Sox2, Rex1, and Sall4) in ES cells (ES), 3 clones of OSK-iPS cells (OSK-iPS 1 to 3), 3 clones of OSK+H1foo-iPS cells (OSKH-iPS 1 to 3), and MEF cells (MEF). The expression levels of pluripotency markers are expressed as values relative to the result of the ES cells, which is 1.

TABLE 5

| Cell | Oct3/4 (Exogenous) | Sox2 (Exogenous) | H1foo (Exogenous) |
|---|---|---|---|
| ES | 0.00 | 0.00 | 0.00 |
| MEF + OSKH | 1.00 | 1.00 | 1.00 |
| OSK-iPS1 | 0.01 | 0.03 | 0.00 |
| OSK-iPS2 | 0.00 | 0.06 | 0.00 |
| OSK-iPS3 | 0.00 | 0.01 | 0.00 |
| OSKH-iPS1 | 0.00 | 0.01 | 0.03 |
| OSKH-iPS2 | 0.00 | 0.01 | 0.05 |
| OSKH-iPS3 | 0.00 | 0.01 | 0.06 |
| MEF | 0.00 | 0.00 | 0.00 |

Table 5 shows the results of analysis of the expression of 3 exogenous proteins (Oct3/4, Sox2, and H1foo) in ES cells (ES), OSKH gene-transduced MEF cells (MEF+OSKH), 3 clones of OSK-iPS cells (OSK-iPS 1 to 3), 3 clones of OSK+H1foo-iPS cells (OSKH-iPS 1 to 3), and MEF cells (MEF). The expression levels of pluripotency markers are expressed as values relative to the result of the OSKH gene-transduced MEF cells, which is taken as 1.

Global gene-transcriptome profiles between the OSK+H1foo-iPS cells and the ES cells or the OSK-iPS cells were compared (FIGS. 4a and b). As a result, it was demonstrated that the gene expression pattern in OSK+H1foo-iPS cells and the gene expression pattern in the ES cells and the OSK-iPS cells are very similar (a correlation coefficient $[R^2]$ of 0.99).

Methylation analysis of genomic DNA was conducted according to the method described in the section of [DNA methylation analysis]. The results demonstrated that DNA in the promoter regions of 2 pluripotency marker (Oct3/4 and Nanog) genes, IG-DMR, and Gt12-DMR were demethylated in the OSK+H1foo-iPS cells as in ES cells and OSK-iPS cells (FIGS. 5a and b). While the demethylation level was found to be heterogeneous among clones (cell groups) of the OSK-iPS cells, such heterogeneity was smaller among the OSK+H1foo-iPS cells (FIGS. 5a and b).

[Properties of EBs Derived from OSK+H1foo-iPS Cells]

To induce the differentiation from iPS cells to various cells, usually, EBs are formed at first and then further differentiation is induced by a method for inducing differentiation specific to the type of cells. Since homogeneity of the number of EBs formed and the EB size has been considered to have an influence on the efficiency of subsequent induction of differentiation, iPS cells that can form a large number of EBs having homogenous sizes have been considered to be desirable. Therefore, the EB formation potency of OSK+H1foo-iPS cells was analyzed.

When the formation of EBs from the OSK+H1foo-iPS cells according to the method described in the section of [embryoid body (EB) formation] above, the EBs derived from such OSK+H1foo-iPS cells are larger in EB number (increase of approximately 12% in percentage) and in EB size ($\mu m^2$) as compared with EBs derived from the OSK-iPS cells (FIGS. 6a to c) and smaller in EB size ($\mu m^2$) variance ($\sigma^2$) (approximately 50% decrease in percentage) (FIGS. 6d and e).

The analysis of the percentage of apoptotic cells according to the method described in the section of [Apoptosis assay] above indicated that the EBs derived from the OSK+H1foo-iPS cells have smaller percentages of early apoptotic cells (annexin V-positive (+)/PI-negative (−) cells) and late apoptotic cells (annexin V (+)/PI (+) cells and annexin V (−)/PI (+) cells) and a higher percentage of viable cells (annexin V (−)/PI (−) cells) as compared with the EBs derived from the OSK-iPS cells (FIGS. 7a and b). The EBs derived from the OSK+H1foo-iPS cells had a percentage of viable cells (annexin V (−)/PI (−) cells) increased to approximately 1.2 times as compared with the EBs derived from the OSK-iPS cells. Moreover, the EBs derived from the OSK+H1foo-iPS cells had a percentage of apoptotic cells (the sum of annexin V (+)/PI (−) cells and annexin V (+)/PI (+) cells) decreased to approximately 0.65 times as compared with the EBs derived from the OSK-iPS cells.

Furthermore, the analysis of iPS cells on the second day from the start of culture in the culture medium for EB formation on the expression of 2 cell proliferation markers (Ki67 and PCNA) according to the method described in the section of [Quantitative RT-PCR analysis] above indicated that the EBs derived from the OSK+H1foo-iPS cells have a higher expression level (increased to approximately 2.4 to 2.6 times) of the cell proliferation markers as compared with the EBs derived from the OSK-iPS cells (FIGS. 8a and b).

The foregoing results indicate that OSK+H1foo-iPS cells form a larger number of EBs with relatively similar sizes and can form EBs with a smaller percentage of dead cells (high-quality EBs) as compared with OSK cells

[Pluripotency of OSK+H1foo-iPS Cells]

The pluripotency of the OSK+H1foo-iPS cells was analyzed. Chimera mice were generated from 2 clones (OSKH1 and 3) of OSK+H1foo-iPS cells that have the normal chromosome number according to the method described in the section of [Co-culture aggregation of ES cells and iPS cells] above. Moreover, as control, chimera mice were generated from 2 clones (OSK1 and 2) of OSK-iPS cells that have the normal chromosome number according to the same method.

Since the iPS cells and ES cells used in this experiment were prepared from somatic cells of black mice, the higher chimera competency of iPS or ES cells results in the generation of blacker mice at higher percentage. As a result of the chimera mice generation study, it was demonstrated that the 2 clones (OSKH1 and 3) of OSK+H1foo-iPS cells have chimera competency equivalent to or higher than the 2 clones (OSK1 and 2) of OSK-iPS cells (FIGS. 9a and b). In particular, OSKH3 was demonstrated to have the chimera competency at the level same as ES cells (FIGS. 9a and b).

Germline transmission potential refers to the potential of pluripotent stem cells such as ES cells and iPS cells to differentiate into germ cells and transmit genes derived from the pluripotent stem cells to the next generation via chimera. This germline transmission potential is one of the most stringent hallmarks of pluripotent stem cells and one of the hallmarks indicating that the pluripotent stem cells are of high quality. Therefore germline transmission potential from 100% chimeric mice was examined by in vitro fertilization (IVF). As a result, the 4 chimeric mice (OSKH1, OSKH3-1, OSKH3-2, and OSKH3-3) derived from OSK+H1foo-iPS cells exhibited higher reproductive potential than the 2 chimeric mice (OSK2-1 and OSK2-2) derived from OSK-iPS cells (FIG. 10a) and generated many pups with colored coats (FIGS. 10b and c). No phenotypic abnormalities were found in these pups.

The foregoing results demonstrated that OSK+H1foo-iPS cells have high pluripotency.

3. Method

[Production of Human iPS Cells and Method for Culturing the Same]

Human iPS cells were produced according to a protocol described in literature (Seki, T., Yuasa, S., Fukuda, K. Generation of induced pluripotent stem cells from a small amount of human peripheral blood using a combination of activated T cells and Sendai virus, Nature Protocols 7, 718-728, 2012). iPS cells (OSKL+H1foo-iPS cells) were produced from human peripheral blood lymphocytes or human skin fibroblasts using a Sendai virus vector containing the human Oct3/4, Sox2, Klf4, L-Myc, and H1foo genes (a nucleotide sequence set forth in SEQ ID No: 1: BC047943). As control, iPS cells (OSKL-iPS cells) were produced using the Azami-Green gene instead of the H1foo gene. This experiment was conducted following the guidelines on gene recombination experimentation at Keio University.

Human iPS cell lines were cultured and maintained on culture plates coated with iMatrix-511 (manufactured by Nippi, Incorporated) in StemFit AK02N (manufactured by Ajinomoto Co., Inc.) culture medium (hereinafter referred to as "human iPS cell culture medium"). The human iPS cell culture medium was replaced every 2 days and the cells were subcultured using StemPro Accutase (manufactured by Gibco) every 5 to 7 days.

4. Results

[Comparison of Expression Level of Genes Reflecting Chromosomal Abnormality in iPS Cells]

To study the genome instability of the established human iPS cells by comparison according to the method described in the section of [Production of human iPS cells and method for culturing the same] above, the expression level of the SRF and ACTG2 genes (Lamm, N., Kerem, B., Genomic Instability in Human Pluripotent Stem Cells Arises from Replicative Stress and Chromosome Condensation Defects Cell Stem Cell 18 (2) 253-261 2016), whose expression level decreases when the cell has chromosomal abnormality, was studied by comparison by quantitative RT-PCR analysis. The quantitative RT-PCR analysis was performed following the method described in the section of [Quantitative RT-PCR analysis] above using 4 clones of OSKL+H1foo-iPS cells and 4 clones of OSKL-iPS cells (control). FIG. 11a shows the results of quantitative RT-PCR analysis on the SRF gene and FIG. 11b shows the results of quantitative RT-PCR analysis on the ACTG2 gene.

As seen from the results of FIGS. 11a and b, the OSKL+H1foo-iPS cell populations also exhibited significantly higher expression level of either of the SRF and ACTG2 genes than the OSKL-iPS cell population (control). These results have demonstrated that use of the H1foo gene, in addition to the nuclear reprogramming substance, suppresses the chromosomal abnormality that may result from the establishment of iPS cells and enables the production of higher-quality iPS cell population.

[Comparison of Expression Level of Undifferentiated State Marker of iPS Cells]

To examine whether iPS cells established according to the method described in the section of [Production of human iPS cells and method for culturing the same] above maintain a stable undifferentiated state, the expression level of the Oct3/4 gene (an undifferentiated state marker of stem cells) was studied by comparison by quantitative RT-PCR analysis. The quantitative RT-PCR analysis was conducted using 4 clones of the OSKL+H1foo-iPS cells and 4 clones of the OSKL-iPS cells (control) following the method described in the section of [Quantitative RT-PCR analysis] above. FIG. 12 shows the results of the quantitative RT-PCR analysis.

As seen from the results of FIG. 12, the OSKL+H1foo-iPS cell population had significantly smaller variance of the expression level of the Oct3/4 gene (undifferentiated state marker in stem cells) among clones as compared with the OSKL-iPS cell population (control). The result indicated that use of the H1foo gene, in addition to the nuclear reprogramming substance, results in the maintenance of a more stable undifferentiated state and enables the production of iPS cell populations with less variance in quality.

[Comparison of Cell Survival Rate in Early Stage after Induction of Differentiation]

To study the number of viable cells in the early stage after the induction of differentiation of human iPS cells established according to the method described in the section of [Production of human iPS cells and method for culturing the same] above, a certain number of cells ($1 \times 10^6$ cells/well) were seeded and then medium was replaced from iPS cell culture medium to RPMI-1640 (manufactured by Sigma Aldrich Co. LLC.)+B27 Supplement (manufactured by Gibco) culture medium, the cells were collected the next day, and the number of viable cells was calculated using a trypan blue solution and compared. FIG. 13 shows the results of such calculation of the number of germ cells conducted for 4 clones of OSKL+H1foo-iPS cells and 4 clones of OSKL-iPS cells (control).

As seen from the results of FIG. 13, the OSKL+H1foo-iPS cell population contained a significantly higher number of viable cells after the induction of differentiation and had a tendency to have higher adaptability to the environment for the induction of differentiation as compared with the OSKL-iPS cell population (control). The result demonstrated that use of the H1foo gene in addition to the nuclear reprogramming substance results in more number of viable cells after the induction of differentiation and allows the production of higher-quality iPS cell populations in that they have higher adaptability to the environment for the induction of differentiation.

[Comparison of Residual Amounts of Undifferentiated State Marker in Early Stage after Induction of Differentiation of iPS Cells]

In the early stage after the induction of differentiation of human iPS cells established according to the method described in the section of [Production of human iPS cells and method for culturing the same] above, the residual amounts of the Oct3/4 gene (undifferentiated state marker of stem cells) were compared. Specifically, a certain number of cells (1×10$^6$ cells/well) were seeded in wells, then medium was replaced from iPS cell culture medium to culture medium for induction of differentiation [DMEM F12 HAM (manufactured by Sigma Aldrich Co. LLC.)+FBS (manufactured by Gibco)+GlutaMAX (manufactured by Gibco)+PenStrep (manufactured by Gibco)+2-mercaptoethanol (manufactured by Sigma Aldrich Co. LLC.)], and cells were collected on the 5th day after the culture medium change to compare the expression level of the Oct3/4 gene, which is an undifferentiated state marker, by quantitative RT-PCR analysis. The quantitative RT-PCR analysis was conducted following the method described in the section of [Quantitative RT-PCR analysis] above using 4 clones of the OSKL+H1foo-iPS cells and 4 clones of the OSKL-iPS cells (control). FIG. 14 shows the results of the quantitative RT-PCR analysis.

As seen from the results of FIG. 14, while the OSKL-iPS cell population (control) had a plurality of clones (OSKL-iPS 2 and OSKL-iPS 4) in which the undifferentiated state marker (Oct3/4) remains high despite being cultured in the culture medium for the induction of differentiation for 5 days, the OSKL+H1foo-iPS cell population had clones any of which expressed the undifferentiated marker at a low level and the valiance of expression of the undifferentiated state marker among clones was significantly smaller. The results demonstrated that the expression of the undifferentiated state marker in the iPS cells produced using the H1foo gene in addition to the nuclear reprogramming substance disappears rapidly when the iPS cells are cultured in the culture medium for the induction of differentiation and the variance of the disappearance is small. Thus, it was demonstrated that use of the H1foo gene in addition to the nuclear reprogramming substance enables the production of iPS cell populations with smaller variance in quality.

INDUSTRIAL APPLICABILITY

The present invention can provide an agent for improving quality of an iPS cell, a method for producing an iPS cell, an iPS cell produced by such a method for production, and a composition for producing an iPS cell. According to the present invention, higher-quality iPS cells with smaller variance in quality can be produced.

The invention claimed is:

1. A method for producing an iPS cell in vitro, comprising:

i) introducing (a) a nuclear reprogramming substance, wherein the nuclear reprogramming substance consists of a polynucleotide encoding an Oct3/4 protein, a polynucleotide encoding a Sox2 protein, and a polynucleotide encoding a Klf4 protein, and (b) a polynucleotide encoding an H1foo protein into a somatic cell, and ii) culturing the somatic cell from i) to produce an iPS cell, wherein the iPS cell, when compared to an iPS cell produced without introducing the polynucleotide encoding an H1foo protein, is improved as shown in one or more selected from the group consisting of the following (1) to (11);

(1) an increase in a percentage of embryoid body formation when iPS cells have been cultured in a culture medium for embryoid body formation;

(2) an increase in a number of embryoid body formation when iPS cells have been cultured in the culture medium for embryoid body formation;

(3) a decrease in a size variance of embryoid bodies when iPS cells have been cultured in the culture medium for embryoid body formation;

(4) an increase in a percentage of viable cells when iPS cells have been cultured in the culture medium for embryoid body formation;

(5) a decrease in a percentage of apoptotic cells when iPS cells have been cultured in the culture medium for embryoid body formation;

(6) an increase in an expression level of a Ki67 gene or a PCNA gene when iPS cells have been cultured in the culture medium for embryoid body formation;

(7) an increase in a chimera competency of iPS cells;
(8) an increase in a germline transmission potential of iPS cells;
(9) an increase in an expression level of a SRF gene in iPS cells;
(10) an increase in an expression level of a ACTG2 gene in iPS cells; and
(11) a decrease in a variance of an expression level of a Oct3/4 gene in iPS cells.

2. An iPS cell produced by the method for producing an iPS cell according to claim 1, wherein the iPS cell, when compared to an iPS cell produced without introducing the polynucleotide encoding an H1foo protein, is improved as shown in one or more selected from the group consisting of the following (1) to (11);
(1) an increase in a percentage of embryoid body formation when iPS cells have been cultured in a culture medium for embryoid body formation;
(2) an increase in a number of embryoid body formation when iPS cells have been cultured in the culture medium for embryoid body formation;
(3) a decrease in a size variance of embryoid bodies when iPS cells have been cultured in the culture medium for embryoid body formation;
(4) an increase in a percentage of viable cells when iPS cells have been cultured in the culture medium for embryoid body formation;
(5) a decrease in a percentage of apoptotic cells when iPS cells have been cultured in the culture medium for embryoid body formation;
(6) an increase in an expression level of a Ki67 gene or a PCNA gene when iPS cells have been cultured in the culture medium for embryoid body formation;
(7) an increase in a chimera competency of iPS cells;
(8) an increase in a germline transmission potential of iPS cells;
(9) an increase in an expression level of a SRF gene in iPS cells;
(10) an increase in an expression level of a ACTG2 gene in iPS cells; and
(11) a decrease in a variance of an expression level of a Oct3/4gene in iPS cells.

3. A method for producing an iPS cell in vitro, comprising:
i) introducing (a) a nuclear reprogramming substance wherein the nuclear reprogramming substance consists of a polynucleotide encoding an Oct3/4 protein, a polynucleotide encoding a Sox2 protein, a polynucleotide encoding a Klf4 protein and a polynucleotide encoding an L-Myc protein, and (b)a polynucleotide encoding an H1foo protein into a somatic cell, and
ii) culturing the somatic cell from i) to produce an iPS cell, wherein the iPS cell, when compared to an iPS cell produced without introducing the polynucleotide encoding an H1foo protein, is improved as shown in one or more selected from the group consisting of the following (1) to (11);
(1) an increase in a percentage of embryoid body formation when iPS cells have been cultured in a culture medium for embryoid body formation;
(2) an increase in a number of embryoid body formation when iPS cells have been cultured in the culture medium for embryoid body formation;
(3) a decrease in a size variance of embryoid bodies when iPS cells have been cultured in the culture medium for embryoid body formation;
(4) an increase in a percentage of viable cells when iPS cells have been cultured in the culture medium for embryoid body formation;
(5) a decrease in a percentage of apoptotic cells when iPS cells have been cultured in the culture medium for embryoid body formation;
(6) an increase in an expression level of a Ki67 gene or a PCNA gene when iPS cells have been cultured in the culture medium for embryoid body formation;
(7) an increase in a chimera competency of iPS cells;
(8) an increase in a germline transmission potential of iPS cells;
(9) an increase in an expression level of a SRF gene in iPS cells;
(10) an increase in an expression level of a ACTG2 gene in iPS cells; and
(11) a decrease in a variance of an expression level of a Oct3/4 gene in iPS cells.

4. An iPS cell produced by the method for producing an iPS cell according to claim 3, wherein the iPS cell, when compared to an iPS cell produced without introducing the polynucleotide encoding an H1foo protein, is improved as shown in one or more selected from the group consisting of the following (1) to (11);
(1) an increase in a percentage of embryoid body formation when iPS cells have been cultured in a culture medium for embryoid body formation;
(2) an increase in a number of embryoid body formation when iPS cells have been cultured in the culture medium for embryoid body formation;
(3) a decrease in a size variance of embryoid bodies when iPS cells have been cultured in the culture medium for embryoid body formation;
(4) an increase in a percentage of viable cells when iPS cells have been cultured in the culture medium for embryoid body formation;
(5) a decrease in a percentage of apoptotic cells when iPS cells have been cultured in the culture medium for embryoid body formation;
(6) an increase in an expression level of a Ki67 gene or a PCNA gene when iPS cells have been cultured in the culture medium for embryoid body formation;
(7) an increase in a chimera competency of iPS cells;
(8) an increase in a germline transmission potential of iPS cells;
(9) an increase in an expression level of a SRF gene in iPS cells;
(10) an increase in an expression level of a ACTG2 gene in iPS cells; and
(11) a decrease in a variance of an expression level of a Oct3/4 gene in iPS cells.

* * * * *

SEQUENCE LISTING

```
<160> NUMBER OF SEQ ID NOS: 60

<210> SEQ ID NO 1
<211> LENGTH: 624
<212> TYPE: DNA
<213> ORGANISM: Homo sapiens
<220> FEATURE:
<221> NAME/KEY: misc_feature
<223> OTHER INFORMATION: Inventor:YUASA, Shinsuke; FUKUDA, Keiichi;
      KUNITOMI, Akira

<400> SEQUENCE: 1 atggccccg cgacggctcc caggagagcg ggtgaggcca aggggaaggg ccccaagaaa        60
ccaagtgagg ccaaggagga ccctcccaac gtgggcaagg tgaaaaaggc agccaagagg      120
ccagcaaagg tgcagaagcc tcctcccaag ccaggcgcag ccacagagaa ggctcgcaag      180
caaggcggcg cggccaagga caccagggca cagtcgggag aggctaggaa ggtgccccc       240 aagccagaca aggccatgcg ggcaccttcc agtgctggtg ggctcagcag gaaggcaaag      300
gccaaaggca gcaggagcag ccaaggagat gctgaggcct acaggaaaac caaagctgag      360
agtaagagtt caaaacccac ggccagcaag gtcaagaatg gtgctgcttc cccgaccaaa      420
aagaaggtgg tggccaaggc caaggcccct aaagctgggc aggggccaaa caccaaggct      480
gctgctcctg ctaagggcag tgggtccaag gtggtacctg cacatttgtc caggaagaca      540
gaggccccca agggccctag aaaggctggg ctgcccatca aggcctcatc atccaaagtg      600
tccagccaga gggctgaagc ttag                                             624

<210> SEQ ID NO 2
<211> LENGTH: 207
<212> TYPE: PRT
<213> ORGANISM: Homo sapiens

<400> SEQUENCE: 2

Met Ala Pro Ala Thr Ala Pro Arg Arg Ala Gly Glu Ala Lys Gly Lys
```

```
        1               5                  10                 15
Gly Pro Lys Lys Pro Ser Glu Ala Lys Glu Asp Pro Pro Asn Val Gly
            20                  25                  30
Lys Val Lys Ala Ala Lys Arg Pro Ala Lys Val Gln Lys Pro Pro
                35                  40                  45
Pro Lys Pro Gly Ala Ala Thr Glu Lys Ala Arg Lys Gln Gly Ala
    50                  55                  60
Ala Lys Asp Thr Arg Ala Gln Ser Gly Glu Ala Arg Lys Val Pro Pro
65                  70                  75                  80
Lys Pro Asp Lys Ala Met Arg Ala Pro Ser Ala Gly Gly Leu Ser
                85                  90                  95
Arg Lys Ala Lys Ala Lys Gly Ser Arg Ser Ser Gln Gly Asp Ala Glu
                100                 105                 110
Ala Tyr Arg Lys Thr Lys Ala Glu Ser Lys Ser Lys Pro Thr Ala
                115                 120                 125
Ser Lys Val Lys Asn Gly Ala Ala Ser Pro Thr Lys Lys Val Val
    130                 135                 140
Ala Lys Ala Lys Ala Pro Lys Ala Gly Gln Gly Pro Asn Thr Lys Ala
145                 150                 155                 160
Ala Ala Pro Ala Lys Gly Ser Gly Ser Lys Val Val Pro Ala His Leu
                165                 170                 175
Ser Arg Lys Thr Glu Ala Pro Lys Gly Pro Arg Lys Ala Gly Leu Pro
                180                 185                 190
Ile Lys Ala Ser Ser Ser Lys Val Ser Ser Gln Arg Ala Glu Ala
                195                 200                 205
```

<210> SEQ ID NO 3
<211> LENGTH: 915
<212> TYPE: DNA
<213> ORGANISM: Mus musculus

<400> SEQUENCE: 3

```
atggctcctg ggagtgtctc cagtgtttct tcctcctctt ttccctccag ggacacatcc      60
ccttctggat catgtgggct ccctggagct gacaagccag gtccaagttg ccgcagaatc     120
caagcaggcc aaaggaaccc aacaatgctg cacatggtgc tagaggcttt gaaggcccgg     180
gaggcacgcc agggcacatc agttgtagcc atcaaggtct acatccaaca caagtacccg     240
acagtggaca ccacccgttt caagtacctg ttgaagcaag ctctggaaac tggcgttcgt     300
cgaggcctcc tcaccaggcc tgctcactcc aaggccaagg gtgccactgg cagcttcaaa     360
ctagttccaa agcccaagac aaagaaagcc tgtgccccca agccggcag ggagctgca      420
ggtgccaagg acaggctc caagaaatct ggattgctga agaaagacca agttggcaag     480
gccacgatgg agaaagggca agaggaggg gcttaccctt gcaaggcagc cacactggag     540
atggcaccta gaaagccaa ggcgaaaccg aagaggtca gaaggctcc cctaaaacaa      600
gacaaagcag caggggcccc tctgactgcc aatggaggcc agaaggtcaa acgcagtggg     660
agcaggcaag aagcaaatgc ccatgggaaa accaaggtg agaaatcgaa gcccttggcc     720
agcaaggtcc agaatagcgt tgcttccctc gccaaaagga gatggcaga catgcccac      780
actgtgacag ttgttcaggg ggctgagaca gtacaggaga ccaaagtgcc cactccttcc     840
caggacatag gacacaaagt acaacccata cctagggtca ggaaggcaaa gaccctgag      900
aacactcagg cctga                                                     915
```

```
<210> SEQ ID NO 4
<211> LENGTH: 304
<212> TYPE: PRT
<213> ORGANISM: Mus musculus

<400> SEQUENCE: 4

Met Ala Pro Gly Ser Val Ser Val Ser Ser Ser Phe Pro Ser
1               5                   10                  15

Arg Asp Thr Ser Pro Ser Gly Ser Cys Gly Leu Pro Gly Ala Asp Lys
            20                  25                  30

Pro Gly Pro Ser Cys Arg Arg Ile Gln Ala Gly Gln Arg Asn Pro Thr
        35                  40                  45

Met Leu His Met Val Leu Glu Ala Leu Lys Ala Arg Glu Ala Arg Gln
    50                  55                  60

Gly Thr Ser Val Val Ala Ile Lys Val Tyr Ile Gln His Lys Tyr Pro
65                  70                  75                  80

Thr Val Asp Thr Thr Arg Phe Lys Tyr Leu Leu Lys Gln Ala Leu Glu
                85                  90                  95

Thr Gly Val Arg Arg Gly Leu Leu Thr Arg Pro Ala His Ser Lys Ala
            100                 105                 110

Lys Gly Ala Thr Gly Ser Phe Lys Leu Val Pro Lys Pro Lys Thr Lys
        115                 120                 125

Lys Ala Cys Ala Pro Lys Ala Gly Arg Gly Ala Ala Gly Ala Lys Glu
    130                 135                 140

Thr Gly Ser Lys Lys Ser Gly Leu Leu Lys Lys Asp Gln Val Gly Lys
145                 150                 155                 160

Ala Thr Met Glu Lys Gly Gln Lys Arg Arg Ala Tyr Pro Cys Lys Ala
                165                 170                 175

Ala Thr Leu Glu Met Ala Pro Lys Lys Ala Lys Ala Lys Pro Lys Glu
            180                 185                 190

Val Arg Lys Ala Pro Leu Lys Gln Asp Lys Ala Ala Gly Ala Pro Leu
        195                 200                 205

Thr Ala Asn Gly Gly Gln Lys Val Lys Arg Ser Gly Ser Arg Gln Glu
    210                 215                 220

Ala Asn Ala His Gly Lys Thr Lys Gly Glu Lys Ser Lys Pro Leu Ala
225                 230                 235                 240

Ser Lys Val Gln Asn Ser Val Ala Ser Leu Ala Lys Arg Lys Met Ala
                245                 250                 255

Asp Met Ala His Thr Val Thr Val Gln Gly Ala Glu Thr Val Gln
            260                 265                 270

Glu Thr Lys Val Pro Thr Pro Ser Gln Asp Ile Gly His Lys Val Gln
        275                 280                 285

Pro Ile Pro Arg Val Arg Lys Ala Lys Thr Pro Glu Asn Thr Gln Ala
    290                 295                 300

<210> SEQ ID NO 5
<211> LENGTH: 21
<212> TYPE: DNA
<213> ORGANISM: Artificial
<220> FEATURE:
<223> OTHER INFORMATION: Nanog-F

<400> SEQUENCE: 5
agggtctgct actgagatgc t                                         21

<210> SEQ ID NO 6
<211> LENGTH: 24
```

```
<212> TYPE: DNA
<213> ORGANISM: Artificial
<220> FEATURE:
<223> OTHER INFORMATION: Nanog-R

<400> SEQUENCE: 6
caacacctgg tttttctgcc accg                                        24

<210> SEQ ID NO 7
<211> LENGTH: 23
<212> TYPE: DNA
<213> ORGANISM: Artificial
<220> FEATURE:
<223> OTHER INFORMATION: endogenous Oct3/4-F

<400> SEQUENCE: 7
tctttccacc aggcccccgg ctc                                         23

<210> SEQ ID NO 8
<211> LENGTH: 23
<212> TYPE: DNA
<213> ORGANISM: Artificial
<220> FEATURE:
<223> OTHER INFORMATION: endogenous Oct3/4-R

<400> SEQUENCE: 8
tgcgggcgga catggggaga tcc                                         23

<210> SEQ ID NO 9
<211> LENGTH: 23
<212> TYPE: DNA
<213> ORGANISM: Artificial
<220> FEATURE:
<223> OTHER INFORMATION: endogenous Sox2-F

<400> SEQUENCE: 9
tagagataga ctccgggcga tga                                         23

<210> SEQ ID NO 10
<211> LENGTH: 23
<212> TYPE: DNA
<213> ORGANISM: Artificial
<220> FEATURE:
<223> OTHER INFORMATION: endogenous Sox2-R

<400> SEQUENCE: 10
ttgccttaaa caagaccacg aaa                                         23

<210> SEQ ID NO 11
<211> LENGTH: 23
<212> TYPE: DNA
<213> ORGANISM: Artificial
<220> FEATURE:
<223> OTHER INFORMATION: exogenous Oct3/4-F

<400> SEQUENCE: 11
ccccagggcc ccattttggt acc                                         23

<210> SEQ ID NO 12
<211> LENGTH: 23
<212> TYPE: DNA
<213> ORGANISM: Artificial
<220> FEATURE:
<223> OTHER INFORMATION: exogenous Oct3/4-R

<400> SEQUENCE: 12
``` cccttttttct ggagactaat aaa                                              23

<210> SEQ ID NO 13
<211> LENGTH: 26
<212> TYPE: DNA
<213> ORGANISM: Artificial
<220> FEATURE:
<223> OTHER INFORMATION: exogenous Sox2-F

<400> SEQUENCE: 13
ggcacccctg gcatggctct tggctc                                            26

<210> SEQ ID NO 14
<211> LENGTH: 24
<212> TYPE: DNA
<213> ORGANISM: Artificial
<220> FEATURE:
<223> OTHER INFORMATION: exogenous Sox2-R

<400> SEQUENCE: 14
ttatcgtcga ccactgtgct gctg                                              24

<210> SEQ ID NO 15
<211> LENGTH: 24
<212> TYPE: DNA
<213> ORGANISM: Artificial
<220> FEATURE:
<223> OTHER INFORMATION: Rex1-F

<400> SEQUENCE: 15
acgagtggca gtttcttctt ggga                                              24

<210> SEQ ID NO 16
<211> LENGTH: 24
<212> TYPE: DNA
<213> ORGANISM: Artificial
<220> FEATURE:
<223> OTHER INFORMATION: Rex1-R

<400> SEQUENCE: 16
tatgactcac ttccaggggg cact                                              24

<210> SEQ ID NO 17
<211> LENGTH: 20
<212> TYPE: DNA
<213> ORGANISM: Artificial
<220> FEATURE:
<223> OTHER INFORMATION: Sall4-F

<400> SEQUENCE: 17
ccctgggaac tgcgatgaag                                                   20

<210> SEQ ID NO 18
<211> LENGTH: 23
<212> TYPE: DNA
<213> ORGANISM: Artificial
<220> FEATURE:
<223> OTHER INFORMATION: Sall4-R

<400> SEQUENCE: 18
tcagagagac taaagaactc ggc                                               23

<210> SEQ ID NO 19
<211> LENGTH: 20
<212> TYPE: DNA
<213> ORGANISM: Artificial

<220> FEATURE:
<223> OTHER INFORMATION: H1foo-F

<400> SEQUENCE: 19
ggcacaggct ttctttgtct                                              20

<210> SEQ ID NO 20
<211> LENGTH: 20
<212> TYPE: DNA
<213> ORGANISM: Artificial
<220> FEATURE:
<223> OTHER INFORMATION: H1foo-R

<400> SEQUENCE: 20
tccaacacaa gtacccgaca                                              20

<210> SEQ ID NO 21
<211> LENGTH: 20
<212> TYPE: DNA
<213> ORGANISM: Artificial
<220> FEATURE:
<223> OTHER INFORMATION: Foxa2-F

<400> SEQUENCE: 21
agcaccatta cgccttcaac                                              20

<210> SEQ ID NO 22
<211> LENGTH: 20
<212> TYPE: DNA
<213> ORGANISM: Artificial
<220> FEATURE:
<223> OTHER INFORMATION: Foxa2-R

<400> SEQUENCE: 22
ccttgaggtc cattttgtgg                                              20

<210> SEQ ID NO 23
<211> LENGTH: 20
<212> TYPE: DNA
<213> ORGANISM: Artificial
<220> FEATURE:
<223> OTHER INFORMATION: Cxcr4-F

<400> SEQUENCE: 23
cgggatgaaa acgtccattt                                              20

<210> SEQ ID NO 24
<211> LENGTH: 21
<212> TYPE: DNA
<213> ORGANISM: Artificial
<220> FEATURE:
<223> OTHER INFORMATION: Cxcr4-R

<400> SEQUENCE: 24
atgaccagga tcaccaatcc a                                            21

<210> SEQ ID NO 25
<211> LENGTH: 22
<212> TYPE: DNA
<213> ORGANISM: Artificial
<220> FEATURE:
<223> OTHER INFORMATION: Col6a2-F

<400> SEQUENCE: 25
ccaccactga aaggaacaac aa                                           22

<210> SEQ ID NO 26
<211> LENGTH: 23
<212> TYPE: DNA
<213> ORGANISM: Artificial
<220> FEATURE:
<223> OTHER INFORMATION: Col6a2-R

<400> SEQUENCE: 26
tccaacacga aatacacgtt gac                                           23

<210> SEQ ID NO 27
<211> LENGTH: 20
<212> TYPE: DNA
<213> ORGANISM: Artificial
<220> FEATURE:
<223> OTHER INFORMATION: T-F

<400> SEQUENCE: 27
tgtcctccct tgttgcctta                                               20

<210> SEQ ID NO 28
<211> LENGTH: 20
<212> TYPE: DNA
<213> ORGANISM: Artificial
<220> FEATURE:
<223> OTHER INFORMATION: T-R

<400> SEQUENCE: 28
atgttccaag ggcagaacag                                               20

<210> SEQ ID NO 29
<211> LENGTH: 20
<212> TYPE: DNA
<213> ORGANISM: Artificial
<220> FEATURE:
<223> OTHER INFORMATION: beta3-Tubulin-F

<400> SEQUENCE: 29
cccagcggca actatgtagg                                               20

<210> SEQ ID NO 30
<211> LENGTH: 19
<212> TYPE: DNA
<213> ORGANISM: Artificial
<220> FEATURE:
<223> OTHER INFORMATION: beta3-Tubulin-R

<400> SEQUENCE: 30
ccagaccgaa cactgtcca                                                19

<210> SEQ ID NO 31
<211> LENGTH: 20
<212> TYPE: DNA
<213> ORGANISM: Artificial
<220> FEATURE:
<223> OTHER INFORMATION: Tubb3-F

<400> SEQUENCE: 31
ccaaatctac ccaccaagga                                               20

<210> SEQ ID NO 32
<211> LENGTH: 20
<212> TYPE: DNA
<213> ORGANISM: Artificial
<220> FEATURE:
<223> OTHER INFORMATION: Tubb3-R

<400> SEQUENCE: 32
agagcttcca gaacgtcgag                                                     20

<210> SEQ ID NO 33
<211> LENGTH: 20
<212> TYPE: DNA
<213> ORGANISM: Artificial
<220> FEATURE:
<223> OTHER INFORMATION: Ki67-F

<400> SEQUENCE: 33
tctgatgtta ggtgtttgag                                                     20

<210> SEQ ID NO 34
<211> LENGTH: 21
<212> TYPE: DNA
<213> ORGANISM: Artificial
<220> FEATURE:
<223> OTHER INFORMATION: Ki67-R

<400> SEQUENCE: 34
cacttttctg gtaacttctt g                                                   21

<210> SEQ ID NO 35
<211> LENGTH: 20
<212> TYPE: DNA
<213> ORGANISM: Artificial
<220> FEATURE:
<223> OTHER INFORMATION: PCNA-F

<400> SEQUENCE: 35
taaagaagag gaggcggtaa                                                     20

<210> SEQ ID NO 36
<211> LENGTH: 20
<212> TYPE: DNA
<213> ORGANISM: Artificial
<220> FEATURE:
<223> OTHER INFORMATION: PCNA-R

<400> SEQUENCE: 36
taagtgtccc atgtcagcaa                                                     20

<210> SEQ ID NO 37
<211> LENGTH: 19
<212> TYPE: DNA
<213> ORGANISM: Artificial
<220> FEATURE:
<223> OTHER INFORMATION: GAPDH-F

<400> SEQUENCE: 37
ttcaacggca cagtcaagg                                                      19

<210> SEQ ID NO 38
<211> LENGTH: 19
<212> TYPE: DNA
<213> ORGANISM: Artificial
<220> FEATURE:
<223> OTHER INFORMATION: GAPDH-R

<400> SEQUENCE: 38
catggactgt ggtcatgag                                                      19

<210> SEQ ID NO 39

-continued

```
<211> LENGTH: 24
<212> TYPE: DNA
<213> ORGANISM: Artificial
<220> FEATURE:
<223> OTHER INFORMATION: Oct3/4-DMR-F

<400> SEQUENCE: 39
ggttttttag aggatggttg agtg                                              24

<210> SEQ ID NO 40
<211> LENGTH: 23
<212> TYPE: DNA
<213> ORGANISM: Artificial
<220> FEATURE:
<223> OTHER INFORMATION: Oct3/4-DMR-R

<400> SEQUENCE: 40
tccaacccta ctacccatc acc                                                23

<210> SEQ ID NO 41
<211> LENGTH: 30
<212> TYPE: DNA
<213> ORGANISM: Artificial
<220> FEATURE:
<223> OTHER INFORMATION: Nanog-DMR-F

<400> SEQUENCE: 41
gattttgtag gtgggattaa ttgtgaattt                                        30

<210> SEQ ID NO 42
<211> LENGTH: 30
<212> TYPE: DNA
<213> ORGANISM: Artificial
<220> FEATURE:
<223> OTHER INFORMATION: Nanog-DMR-R

<400> SEQUENCE: 42
accaaaaaaa cccacactca tatcaatata                                        30

<210> SEQ ID NO 43
<211> LENGTH: 22
<212> TYPE: DNA
<213> ORGANISM: Artificial
<220> FEATURE:
<223> OTHER INFORMATION: IG-DMR-F

<400> SEQUENCE: 43
gtggtttgtt atgggtaagt tt                                                22

<210> SEQ ID NO 44
<211> LENGTH: 24
<212> TYPE: DNA
<213> ORGANISM: Artificial
<220> FEATURE:
<223> OTHER INFORMATION: IG-DMR-R

<400> SEQUENCE: 44
cccttccctc actccaaaaa ttaa                                              24

<210> SEQ ID NO 45
<211> LENGTH: 28
<212> TYPE: DNA
<213> ORGANISM: Artificial
<220> FEATURE:
<223> OTHER INFORMATION: Gtl2-DMR-F

<400> SEQUENCE: 45
```
agttattttt tgtttgaaag gatgtgta                                              28

<210> SEQ ID NO 46
<211> LENGTH: 28
<212> TYPE: DNA
<213> ORGANISM: Artificial
<220> FEATURE:
<223> OTHER INFORMATION: Gtl2-DMR-R

<400> SEQUENCE: 46
ctaactttaa aaaaaaatcc ccaacact                                              28

<210> SEQ ID NO 47
<211> LENGTH: 1083
<212> TYPE: DNA
<213> ORGANISM: Homo sapiens

<400> SEQUENCE: 47
atggcgggac acctggcttc ggatttcgcc ttctcgcccc ctccaggtgg tggaggtgat            60
gggccagggg ggccggagcc gggctgggtt gatcctcgga cctggctaag cttccaaggc           120
cctcctggag ggccaggaat cgggccgggg gttgggccag gctctgaggt gtggggatt            180
cccccatgcc ccccgccgta tgagttctgt gggggatgg cgtactgtgg ccccaggtt            240
ggagtggggc tagtgcccca aggcggcttg gagacctctc agcctgaggg cgaagcagga           300
gtcggggtgg agagcaactc cgatggggcc tccccggagc cctgcaccgt caccctggt            360
gccgtgaagc tggagaagga gaagctggag caaaacccgg aggagtccca ggacatcaaa           420
gctctgcaga aagaactcga gcaatttgcc aagctcctga gcagaagag gatcaccctg            480
ggatatacac aggccgatgt ggggctcacc ctggggggttc tatttgggaa ggtattcagc          540
caaacgacca tctgccgctt tgaggctctg cagcttagct tcaagaacat gtgtaagctg           600
cggcccttgc tgcagaagtg ggtggaggaa gctgacaaca atgaaaatct tcaggagata           660
tgcaaagcag aaaccctcgt gcaggcccga agagaaagc gaaccagtat cgagaaccga            720
gtgagaggca acctggagaa tttgttcctg cagtgcccga aaccacact gcagcagatc            780
agccacatcg cccagcagct tgggctcgag aaggatgtgg tccgagtgtg gttctgtaac           840
cggcgccaga agggcaagcg atcaagcagc gactatgcac aacgagagga ttttgaggct           900
gctgggtctc ctttctcagg ggaccagtg tcctttcctc tggccccagg ccccattttt            960
ggtaccccag gctatgggag ccctcacttc actgcactgt actcctcggt cccttttccct         1020
gaggggggaag ccttttcccc tgtctccgtc accactctgg gctctcccat gcattcaaac         1080
tga                                                                       1083

<210> SEQ ID NO 48
<211> LENGTH: 360
<212> TYPE: PRT
<213> ORGANISM: Homo sapiens

<400> SEQUENCE: 48

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro

|   |   |   |   |   |   |   |   |   |   |   |   |
|---|---|---|---|---|---|---|---|---|---|---|---|
| Pro | Pro | Tyr | Glu | Phe | Cys | Gly | Gly | Met | Ala | Tyr | Cys | Gly | Pro | Gln | Val |
| 65 |  |  |  | 70 |  |  |  | 75 |  |  |  | 80 |

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
            130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
                180                 185                 190

Ser Phe Lys Asn Met Cys Lys Leu Arg Pro Leu Leu Gln Lys Trp Val
                195                 200                 205

Glu Glu Ala Asp Asn Asn Glu Asn Leu Gln Glu Ile Cys Lys Ala Glu
            210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
                260                 265                 270

Val Val Arg Val Trp Phe Cys Asn Arg Arg Gln Lys Gly Lys Arg Ser
                275                 280                 285

Ser Ser Asp Tyr Ala Gln Arg Glu Asp Phe Glu Ala Ala Gly Ser Pro
            290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
                340                 345                 350

Leu Gly Ser Pro Met His Ser Asn
            355                 360

<210> SEQ ID NO 49
<211> LENGTH: 954
<212> TYPE: DNA
<213> ORGANISM: Homo sapiens

<400> SEQUENCE: 49
atgtacaaca tgatggagac ggagctgaag ccgccgggcc cgcagcaaac ttcgggggc     60 ggcggcggca actccaccgc ggcggcggcc ggcggcaacc agaaaaacag cccggaccgc    120
gtcaagcggc ccatgaatgc cttcatggtg tggtcccgcg gcagcggcg caagatggcc    180 caggagaacc ccaagatgca caactcggag atcagcaagc gcctgggcgc cgagtggaaa    240
cttttgtcgg agacggagaa gcggccgttc atcgacgagg ctaagcggct gcgagcgctg    300
cacatgaagg agcacccgga ttataaatac cggccccggc ggaaaaccaa gacgctcatg    360

```
aagaaggata agtacacgct gcccggcggg ctgctggccc ccggcggcaa tagcatggcg    420
agcggggtcg gggtgggcgc cggcctgggc gcgggcgtga accagcgcat ggacagttac    480
gcgcacatga acggctggag caacggcagc tacagcatga tgcaggacca gctgggctac    540
ccgcagcacc cgggcctcaa tgcgcacggc gcagcgcaga tgcagcccat gaccgctac    600 gacgtgagcg ccctgcagta caactccatg accagctcgc agacctacat gaacggctcg    660
cccacctaca gcatgtccta ctcgcagcag ggcaccctg gcatggctct tggctccatg     720
ggttcggtgg tcaagtccga ggccagctcc agccccctg tggttacctc ttcctcccac     780
tccagggcgc cctgccaggc cggggacctc cgggacatga tcagcatgta tctccccggc    840
gccgaggtgc cggaacccgc cgcccccagc agacttcaca tgtcccagca ctaccagagc    900
ggcccggtgc ccggcacggc cattaacggc acactgcccc tctcacacat gtga          954
```

```
<210> SEQ ID NO 50
<211> LENGTH: 317
<212> TYPE: PRT
<213> ORGANISM: Homo sapiens

<400> SEQUENCE: 50

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Val Val Thr
                245                 250                 255

Ser Ser Ser His Ser Arg Ala Pro Cys Gln Ala Gly Asp Leu Arg Asp
            260                 265                 270
```

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
        290                 295                 300

Gly Thr Ala Ile Asn Gly Thr Leu Pro Leu Ser His Met
305                 310                 315

<210> SEQ ID NO 51
<211> LENGTH: 1440
<212> TYPE: DNA
<213> ORGANISM: Homo sapiens

<400> SEQUENCE: 51

```
atgaggcagc cacctggcga gtctgacatg gctgtcagcg acgcgctgct cccatctttc      60
tccacgttcg cgtctggccc ggcgggaagg gagaagacac tgcgtcaagc aggtgccccg     120
aataaccgct ggcgggagga gctctcccac atgaagcgac ttcccccagt gcttcccggc     180
cgccccatg acctggcggc ggcgaccgtg ccacagacc tggagagcgg cggagccggt      240
gcggcttgcg gcggtagcaa cctggcgccc ctacctcgga gagagaccga ggagttcaac     300
gatctcctgg acctggactt tattctctcc aattcgctga cccatcctcc ggagtcagtg     360
gccgccaccg tgtcctcgtc agcgtcagcc tcctcttcgt cgtcgccgtc gagcagcggc     420
cctgccagcg cgcccctccac ctgcagcttc acctatccga tcgggccgg gaacgacccg     480
ggcgtggcgc cgggcggcac gggcggaggc ctcctctatg cagggagtc cgctccccct     540
ccgacggctc ccttcaacct ggcggacatc aacgacgtga gccctcggg cggcttcgtg     600
gccgagctcc tgcggccaga attggacccg gtgtacattc cgccgcagca gccgcagccg     660
ccaggtggcg ggctgatggg caagttcgtg ctgaaggcgt cgctgagcgc cctggcagc     720
gagtacggca gcccgtcggt catcagcgtc agcaaaggca gccctgacgg cagccacccg     780
gtggtggtgg cgccctacaa cggcgggccg ccgcgcacgt gccccaagat caagcaggag     840
gcggtctctt cgtgcaccca cttgggcgct ggaccccctc tcagcaatgg ccaccggccg     900
gctgcacacg acttcccccct ggggcggcag ctccccagca ggactacccc gaccctgggt     960
cttgaggaag tgctgagcag cagggactgt caccctgccc tgccgcttcc tcccggcttc    1020
catccccacc cggggcccaa ttacccatcc ttcctgcccg atcagatgca gccgcaagtc    1080
ccgccgctcc attaccaaga gctcatgcca cccggttcct gcatgccaga ggagcccaag    1140
ccaaagaggg gaagacgatc gtggcccccgg aaaaggaccg ccacccacac ttgtgattac    1200
gcgggctgcg gcaaaaccta cacaaagagt tcccatctca aggcacacct gcgaacccac    1260
acaggtgaga aaccttacca ctgtgactgg gacggctgtg gatggaaatt cgcccgctca    1320
gatgaactga ccaggcacta ccgtaaacac acggggcacc gcccgttcca gtgccaaaaa    1380
tgcgaccgag cattttccag gtcggaccac ctcgccttac acatgaagag gcatttttaa    1440
```

<210> SEQ ID NO 52
<211> LENGTH: 479
<212> TYPE: PRT
<213> ORGANISM: Homo sapiens

<400> SEQUENCE: 52

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

```
Thr Leu Arg Gln Ala Gly Ala Pro Asn Asn Arg Trp Arg Glu Glu Leu
         35                  40                  45

Ser His Met Lys Arg Leu Pro Pro Val Leu Pro Gly Arg Pro Tyr Asp
 50                  55                  60

Leu Ala Ala Ala Thr Val Ala Thr Asp Leu Glu Ser Gly Gly Ala Gly
 65                  70                  75                  80

Ala Ala Cys Gly Gly Ser Asn Leu Ala Pro Leu Pro Arg Arg Glu Thr
                 85                  90                  95

Glu Glu Phe Asn Asp Leu Leu Asp Leu Asp Phe Ile Leu Ser Asn Ser
             100                 105                 110

Leu Thr His Pro Pro Glu Ser Val Ala Ala Thr Val Ser Ser Ser Ala
         115                 120                 125

Ser Ala Ser Ser Ser Ser Ser Pro Ser Ser Gly Pro Ala Ser Ala
 130                 135                 140

Pro Ser Thr Cys Ser Phe Thr Tyr Pro Ile Arg Ala Gly Asn Asp Pro
145                 150                 155                 160

Gly Val Ala Pro Gly Thr Gly Gly Leu Leu Tyr Gly Arg Glu
                 165                 170                 175

Ser Ala Pro Pro Pro Thr Ala Pro Phe Asn Leu Ala Asp Ile Asn Asp
                 180                 185                 190

Val Ser Pro Ser Gly Gly Phe Val Ala Glu Leu Leu Arg Pro Glu Leu
     195                 200                 205

Asp Pro Val Tyr Ile Pro Pro Gln Gln Pro Gln Pro Pro Gly Gly Gly
         210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                 245                 250                 255

Gly Ser His Pro Val Val Ala Pro Tyr Asn Gly Gly Pro Pro Arg
                 260                 265                 270

Thr Cys Pro Lys Ile Lys Gln Glu Ala Val Ser Ser Cys Thr His Leu
                 275                 280                 285

Gly Ala Gly Pro Pro Leu Ser Asn Gly His Arg Pro Ala Ala His Asp
 290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                 325                 330                 335

Pro Pro Gly Phe His Pro His Pro Gly Pro Asn Tyr Pro Ser Phe Leu
                 340                 345                 350

Pro Asp Gln Met Gln Pro Gln Val Pro Pro Leu His Tyr Gln Glu Leu
                 355                 360                 365

Met Pro Pro Gly Ser Cys Met Pro Glu Glu Pro Lys Pro Lys Arg Gly
         370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                 405                 410                 415

Leu Arg Thr His Thr Gly Glu Lys Pro Tyr His Cys Asp Trp Asp Gly
                 420                 425                 430

Cys Gly Trp Lys Phe Ala Arg Ser Asp Glu Leu Thr Arg His Tyr Arg
         435                 440                 445

Lys His Thr Gly His Arg Pro Phe Gln Cys Gln Lys Cys Asp Arg Ala
```

450                 455                 460
Phe Ser Arg Ser Asp His Leu Ala Leu His Met Lys Arg His Phe
465                 470                 475

<210> SEQ ID NO 53
<211> LENGTH: 1095
<212> TYPE: DNA
<213> ORGANISM: Homo sapiens

<400> SEQUENCE: 53

| | |
|---|---|
| atggactacg actcgtacca gcactatttc tacgactatg actgcgggga ggatttctac | 60 |
| cgctccacgg cgcccagcga ggacatctgg aagaaattcg agctggtgcc atcgcccccc | 120 |
| acgtcgccgc cctggggctt gggtcccggc gcaggggacc cggcccccgg gattggtccc | 180 |
| ccggagccgt ggcccggagg gtgcaccgga gacgaagcgg aatcccgggg ccactcgaaa | 240 |
| ggctggggca ggaactacgc ctccatcata cgccgtgact gcatgtggag cggcttctcg | 300 |
| gcccgggaac ggctggagag agctgtgagc gaccggctcg ctcctggcgc gccccggggg | 360 |
| aacccgccca aggcgtccgc cgccccggac tgcactccca gcctcgaagc cggcaacccg | 420 |
| gcgcccgccg ccccctgtcc gctgggcgaa cccaagaccc aggcctgctc cgggtccgag | 480 |
| agcccaagcg actcggagaa tgaagaaatt gatgttgtga cagtagagaa gaggcagtct | 540 |
| ctgggtattc ggaagccggt caccatcacg gtgcgagcag accccctgga tccctgcatg | 600 |
| aagcatttcc acatctccat ccatcagcaa cagcacaact atgctgcccg ttttcctcca | 660 |
| gaaagctgct cccaagaaga ggcttcagag aggggtcccc aagaagaggt tctggagaga | 720 |
| gatgctgcag gggaaaagga agatgaggag gatgaagaga ttgtgagtcc cccacctgta | 780 |
| gaaagtgagg ctgcccagtc ctgccacccc aaacctgtca gttctgatac tgaggatgtg | 840 |
| accaagagga gaatcacaa cttcctggag cgcaagaggc ggaatgacct gcgttcgcga | 900 |
| ttcttggcgc tgagggacca ggtgcccacc ctggccagct gctccaaggc ccccaaagta | 960 |
| gtgatcctaa gcaaggcctt ggaatacttg caagccctgg tggggctga aagaggatg | 1020 |
| gctacagaga aaagacagct ccgatgccgg cagcagcagt tgcagaaaag aattgcatac | 1080 |
| ctcactggct actaa | 1095 |

<210> SEQ ID NO 54
<211> LENGTH: 364
<212> TYPE: PRT
<213> ORGANISM: Homo sapiens

<400> SEQUENCE: 54

Met Asp Tyr Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Thr Ser Pro Pro Trp Gly Leu Gly
        35                  40                  45

Pro Gly Ala Gly Asp Pro Ala Pro Gly Ile Gly Pro Pro Glu Pro Trp
    50                  55                  60

Pro Gly Gly Cys Thr Gly Asp Glu Ala Glu Ser Arg Gly His Ser Lys
65                  70                  75                  80

Gly Trp Gly Arg Asn Tyr Ala Ser Ile Ile Arg Arg Asp Cys Met Trp
                85                  90                  95

Ser Gly Phe Ser Ala Arg Glu Arg Leu Glu Arg Ala Val Ser Asp Arg
            100                 105                 110

Leu Ala Pro Gly Ala Pro Arg Gly Asn Pro Pro Lys Ala Ser Ala Ala
            115                 120                 125

Pro Asp Cys Thr Pro Ser Leu Glu Ala Gly Asn Pro Ala Pro Ala Ala
        130                 135                 140

Pro Cys Pro Leu Gly Glu Pro Lys Thr Gln Ala Cys Ser Gly Ser Glu
145                 150                 155                 160

Ser Pro Ser Asp Ser Glu Asn Glu Glu Ile Asp Val Thr Val Glu
                165                 170                 175

Lys Arg Gln Ser Leu Gly Ile Arg Lys Pro Val Thr Ile Thr Val Arg
                180                 185                 190

Ala Asp Pro Leu Asp Pro Cys Met Lys His Phe His Ile Ser Ile His
            195                 200                 205

Gln Gln Gln His Asn Tyr Ala Ala Arg Phe Pro Pro Glu Ser Cys Ser
        210                 215                 220

Gln Glu Glu Ala Ser Glu Arg Gly Pro Gln Glu Val Leu Glu Arg
225                 230                 235                 240

Asp Ala Ala Gly Glu Lys Glu Asp Glu Asp Glu Ile Val Ser
                245                 250                 255

Pro Pro Pro Val Glu Ser Glu Ala Ala Gln Ser Cys His Pro Lys Pro
            260                 265                 270

Val Ser Ser Asp Thr Glu Asp Val Thr Lys Arg Lys Asn His Asn Phe
            275                 280                 285

Leu Glu Arg Lys Arg Arg Asn Asp Leu Arg Ser Arg Phe Leu Ala Leu
            290                 295                 300

Arg Asp Gln Val Pro Thr Leu Ala Ser Cys Ser Lys Ala Pro Lys Val
305                 310                 315                 320

Val Ile Leu Ser Lys Ala Leu Glu Tyr Leu Gln Ala Leu Val Gly Ala
                325                 330                 335

Glu Lys Arg Met Ala Thr Glu Lys Arg Gln Leu Arg Cys Arg Gln Gln
                340                 345                 350

Gln Leu Gln Lys Arg Ile Ala Tyr Leu Thr Gly Tyr
        355                 360

<210> SEQ ID NO 55
<211> LENGTH: 20
<212> TYPE: DNA
<213> ORGANISM: Artificial
<220> FEATURE:
<223> OTHER INFORMATION: SRF-F

<400> SEQUENCE: 55
acccataagc cccagctatc          20

<210> SEQ ID NO 56
<211> LENGTH: 20
<212> TYPE: DNA
<213> ORGANISM: Artificial
<220> FEATURE:
<223> OTHER INFORMATION: SRF-R

<400> SEQUENCE: 56
ggtgccaaga tggaagtcac          20

<210> SEQ ID NO 57
<211> LENGTH: 20
<212> TYPE: DNA
<213> ORGANISM: Artificial
<220> FEATURE:

<223> OTHER INFORMATION: ACTG2-F

<400> SEQUENCE: 57
cggtggtctc ctcttcacac                                            20

<210> SEQ ID NO 58
<211> LENGTH: 22
<212> TYPE: DNA
<213> ORGANISM: Artificial
<220> FEATURE:
<223> OTHER INFORMATION: ACTG2-R

<400> SEQUENCE: 58
cactgggaga agaacctctc at                                         22

<210> SEQ ID NO 59
<211> LENGTH: 1041
<212> TYPE: DNA
<213> ORGANISM: Homo sapiens

<400> SEQUENCE: 59
atggctcctg ggagcgtcac cagcgacatc tcaccctcct cgacttccac agcaggatca    60
tccaggtctc ctgaatctga aaagccaggc ccgagccacg gcggtgtccc accaggaggc   120
ccgagccaca gcagcctccc ggtgggacgc cgccaccccc cggtgctacg catggtgctg   180
gaggcgctgc aggctgggga gcagcgccgg ggcacgtcgg tggcagctat caagctctac   240
atcctgcaca gtacccaac agtggacgtc ctccgcttca gtacctgct gaagcaggcg     300
ctggccactg gcatgcgccg tggcctcctc gccaggcccc tcaactccaa agccaggggg   360
gccactggca gcttcaaatt agttcccaag cacaagaaga aaatccagcc caggaagatg   420
gccccgcga cggctcccag gagagcgggt gaggccaagg ggaagggccc caagaaacca     480
agtgaggcca aggaggaccc tcccaacgtg ggcaaggtga aaaggcagc caagaggcca     540
gcaaaggtgc agaagcctcc tcccaagcca ggcgcagcca cagagaaggc tcgcaagcaa   600
ggcggcgcgg ccaaggacac cagggcacag tcgggagagg ctaggaaggt gcccccaag    660
ccagacaagg ccatgcgggc accttccagt gctggtgggc tcagcaggaa ggcaaaggcc   720
aaaggcagca ggagcagcca aggagatgct gaggcctaca ggaaaaccaa agctgagagt   780
aagagttcaa aacccacggc cagcaaggtc aagaatggtg ctgcttcccc gaccaaaaag   840
aaggtggtgg ccaaggccaa ggcccctaaa gctgggcagg ggccaaacac caaggctgct   900
gctcctgcta agggcagtgg gtccaaggtg gtacctgcac atttgtccag gaagacagag   960
gcccccaagg gccctagaaa ggctgggctg cccatcaagg cctcatcatc caaagtgtcc  1020
agccagaggg ctgaagctta g                                           1041

<210> SEQ ID NO 60
<211> LENGTH: 346
<212> TYPE: PRT
<213> ORGANISM: Homo sapiens

<400> SEQUENCE: 60

Met Ala Pro Gly Ser Val Thr Ser Asp Ile Ser Pro Ser Ser Thr Ser
1               5                   10                  15

Thr Ala Gly Ser Ser Arg Ser Pro Glu Ser Glu Lys Pro Gly Pro Ser
                20                  25                  30

His Gly Gly Val Pro Pro Gly Gly Pro Ser His Ser Ser Leu Pro Val
            35                  40                  45

```
Gly Arg Arg His Pro Pro Val Leu Arg Met Val Leu Glu Ala Leu Gln
 50                  55                  60
Ala Gly Glu Gln Arg Arg Gly Thr Ser Val Ala Ala Ile Lys Leu Tyr
 65              70                  75                  80
Ile Leu His Lys Tyr Pro Thr Val Asp Val Leu Arg Phe Lys Tyr Leu
                 85                  90                  95
Leu Lys Gln Ala Leu Ala Thr Gly Met Arg Arg Gly Leu Leu Ala Arg
                100             105                 110
Pro Leu Asn Ser Lys Ala Arg Gly Ala Thr Gly Ser Phe Lys Leu Val
            115             120                 125
Pro Lys His Lys Lys Lys Ile Gln Pro Arg Lys Met Ala Pro Ala Thr
            130             135             140
Ala Pro Arg Arg Ala Gly Glu Ala Lys Gly Lys Gly Pro Lys Lys Pro
145                 150             155                 160
Ser Glu Ala Lys Glu Asp Pro Pro Asn Val Gly Lys Val Lys Lys Ala
                165             170             175
Ala Lys Arg Pro Ala Lys Val Gln Lys Pro Pro Pro Lys Pro Gly Ala
            180             185             190
Ala Thr Glu Lys Ala Arg Lys Gln Gly Gly Ala Ala Lys Asp Thr Arg
        195             200             205
Ala Gln Ser Gly Glu Ala Arg Lys Val Pro Pro Lys Pro Asp Lys Ala
        210             215             220
Met Arg Ala Pro Ser Ser Ala Gly Gly Leu Ser Arg Lys Ala Lys Ala
225             230             235                 240
Lys Gly Ser Arg Ser Ser Gln Gly Asp Ala Glu Ala Tyr Arg Lys Thr
            245             250                 255
Lys Ala Glu Ser Lys Ser Ser Lys Pro Thr Ala Ser Lys Val Lys Asn
            260             265             270
Gly Ala Ala Ser Pro Thr Lys Lys Lys Val Val Ala Lys Ala Lys Ala
            275             280             285
Pro Lys Ala Gly Gln Gly Pro Asn Thr Lys Ala Ala Ala Pro Ala Lys
        290             295             300
Gly Ser Gly Ser Lys Val Val Pro Ala His Leu Ser Arg Lys Thr Glu
305             310             315                 320
Ala Pro Lys Gly Pro Arg Lys Ala Gly Leu Pro Ile Lys Ala Ser Ser
                325             330             335
Ser Lys Val Ser Ser Gln Arg Ala Glu Ala
            340             345
```